the present invention relates to novel substituted pyridines/pyrimidines of the formula I

United States Patent
Braun et al.

(10) Patent No.: US 6,265,398 B1
(45) Date of Patent: Jul. 24, 2001

(54) SUBSTITUTED PYRIDINES/PYRIMIDINES, THEIR PREPARATION AND THEIR USE AS PESTICIDES

(75) Inventors: Ralf Braun, Dernbach; Wolfgang Schaper, Diedorf; Herbert Stark, Kelkheim; Rainer Preuss, Berlin; Werner Knauf, Liederbach; Ulrich Sanft, Hofheim; Manfred Kern, Lörzweiler; Werner Bonin, Kelkheim, all of (DE)

(73) Assignee: Hoechst Schering AgrEvo GmbH, Frankfurt am Main (DE)

( * ) Notice: Subject to any disclaimer, the term of this patent is extended or adjusted under 35 U.S.C. 154(b) by 0 days.

(21) Appl. No.: 09/177,395

(22) Filed: Oct. 23, 1998

Related U.S. Application Data

(63) Continuation of application No. 08/843,151, filed on Apr. 11, 1997, now abandoned.

(30) Foreign Application Priority Data

Apr. 15, 1996 (DE) ............................................. 196 14 718

(51) Int. Cl.[7] ........................ A61K 31/506; A61K 31/54; C07D 239/24; C07D 403/06; C07D 403/12
(52) U.S. Cl. ........................... 514/222.5; 514/256; 544/2; 544/8; 544/182; 544/316; 544/317; 544/318; 544/319; 546/290; 546/297
(58) Field of Search ....................... 544/316, 319, 544/317, 318, 182, 2, 8; 514/256, 222.5

(56) References Cited

U.S. PATENT DOCUMENTS

| 3,470,182 | 9/1969 | Hardtmann et al. ................. 546/287 |
| 5,571,815 | 11/1996 | Schaper et al. ....................... 544/298 |

FOREIGN PATENT DOCUMENTS

WO 93/19050   9/1993  (WO).

OTHER PUBLICATIONS

Chemical Abstracts, vol. 124, No. 11, 1996, Abstract No. 13494u, A.J. Bridges et al.
Biorgan. Med. Chem., Bd. 3, No. 12, 1995, USA pp. 1651–1656.

Primary Examiner—Richard L. Raymond
Assistant Examiner—Venkataraman Balasubramanian
(74) Attorney, Agent, or Firm—Frommer Lawrence & Haug LLP

(57) ABSTRACT

The present invention relates to novel substituted pyridines/pyrimidines of the formula I

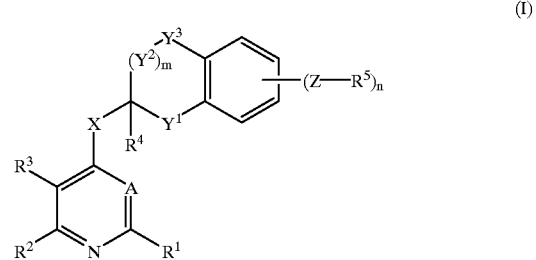

(I)

where

A is CH or N;

X is NH, O or $S(O)_q$ where q is 0, 1 or 2;

$Y^1$, $Y^2$ and $Y^3$ independently of one another are a group of the formula —O—, —CO—, —$CNR^6$—, —$S(O)_r$— or —$N(O)_lR^6$— where l is 0 or 1 and where r is 0, 1 or 2, or a group of the formula $CR^7R^8$, or $Y^1$ or $Y^3$ replace a direct bond;

Z is a direct bond, $NR^9$, O, $S(O)_s$ where s is 0, 1 or 2, $OSO_2$, $SO_2O$, $NR^{10}SO_2$, $SO_2NR^{11}$, $SiR^{12}R^{13}$ or

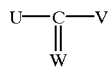

where U is a direct bond, $NR^{14}$ or O;

W is oxygen or sulfur;

V is a direct bond, $NR^{15}$ or oxygen;

m and n and 0, 1, 2, 3 or 4; where the radicals $R^1$ to $R^{15}$ have the meaning given in the description, to processes for their preparation, to their use as pesticides, fungicides and ovicides and to their use as veterinary medicaments.

13 Claims, No Drawings

SUBSTITUTED PYRIDINES/PYRIMIDINES, THEIR PREPARATION AND THEIR USE AS PESTICIDES

This application is a continuation of application U.S. Ser. No. 08/843,151, filed Apr. 11, 1997 now abandoned.

The invention relates to novel substituted pyridines/pyrimidines, to processes for their preparation, and to their use as pesticides, fungicides and ovicides.

It has already been disclosed that certain cycloalkylamino and -alkoxy heterocycles have a fungicidal, acaricidal and insecticidal activity (U.S. Pat. No. 5,571,815). However, the biological activity of these compounds is not satisfactory for all exemples of use, in particular when low rates and concentrations are applied.

There have been found novel substituted pyridines/pyrimidines of the formula I

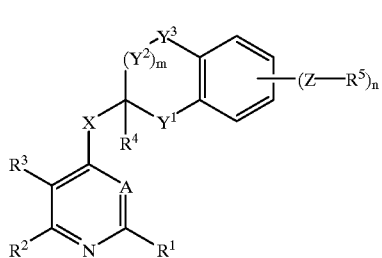

(I)

in which the radicals and groups are as defined below and which are highly suitable for controlling animal pests such as insects, arachnids, nematodes, helminths and molluscs and eggs of these, for controlling endo- and ectoparasites in the field of veterinary medicine and for controlling harmful fungi while showing good plant tolerance and favorable toxicity to warm-blooded species.

The invention therefore relates to compounds of the formula I in which $R^1$ is hydrogen, halogen, $(C_1-C_4)$-alkyl, $(C_1-C_4)$-haloalkyl or $(C_3-C_5)$-cycloalkyl;

$R^2$ and $R^3$ are identical or different and are in each case hydrogen, $(C_1-C_4)$-alkyl, $(C_1-C_4)$-haloalkyl, $(C_2-C_4)$-alkenyl, $(C_2-C_4)$-haloalkenyl, $(C_2-C_4)$-alkynyl, $(C_2-C_4)$-haloalkynyl, tri-$(C_1-C_4)$-alkylsilyl-$(C_2-C_4)$-alkynyl, $(C_1-C_4)$-alkoxy, $(C_1-C_4)$-haloalkoxy, $(C_1-C_4)$-alkoxy-$(C_1-C_4)$-alkyl, $(C_1-C_4)$-haloalkoxy-$(C_1-C_4)$-alkyl, $(C_1-C_4)$-alkoxy-$(C_1-C_4)$-haloalkyl, $(C_1-C_4)$-haloalkoxy-$(C_1-C_4)$-haloalkyl, halogen, hydroxyl, $(C_1-C_4)$-hydroxyalkyl, $(C_1-C_4)$-alkanoyl, $(C_1-C_4)$-alkanoyl-$(C_1-C_4)$-alkyl, $(C_2-C_4)$-haloalkanoyl, $(C_3-C_5)$-cycloalkyl, $(C_4-C_5)$-cycloalkenyl, $(C_3-C_5)$-cycloalkoxy, $(C_3-C_5)$-halocycloalkyl, $(C_4-C_5)$-halocycloalkenyl, cyano, $(C_1-C_4)$-cyanoalkyl, nitro, $(C_1-C_4)$-nitroalkyl, thiocyano, $(C_1-C_4)$-thiocyanoalkyl, $(C_1-C_4)$-alkoxycarbonyl, $(C_1-C_4)$-alkoxycarbonyl-$(C_1-C_4)$-alkyl, $(C_1-C_4)$-haloalkoxycarbonyl, $(C_1-C_4)$ alkanoyloxy-$(C_1-C_4)$-alkyl, $(C_1-C_4)$-alkylthio $(C_1-C_4)$-alkylthio-$(C_1-C_4)$-alkyl, $(C_1-C_4)$-haloalkylthio, $(C_1-C_4)$-alkylsulfinyl, $(C_1-C_4)$-haloalkylsulfinyl, $(C_1-C_4)$-alkylsulfonyl or $(C_1-C_4)$-haloalkylsulfonyl; or $R^2$ and $R^3$ together with the carbon atoms to which they are bonded form an unsaturated 5- or 6-membered carbocyclic ring which, if it is a 5-membered ring, can contain an oxygen or sulfur atom instead of $CH_2$ or which, if it is a 6-membered ring, can contain one or two nitrogen atoms instead of one or two CH units and which is optionally substituted by 1, 2 or 3 identical or different radicals $R^{27}$, or $R^2$ and $R^3$ together with the carbon atoms to which they are bonded form a saturated 5-, 6- or 7-membered carbocyclic ring which can contain oxygen and/or sulfur instead of one or two $CH_2$ groups and which is optionally substituted by 1, 2 or 3 $(C_1-C_4)$-alkyl groups;

A is CH or N;

X is NH, O or $S(O)_q$ where q is 0, 1 or 2;

$Y^1$, $Y^2$ and $Y^3$ independently of one another are a group of the formula —O—, —CO—, —CNR$^6$—, —S(O)$_r$—, —N(O)$_l$R$^6$— or $CR^7R^8$ where r is 0, 1 or 2 and l is 0 or 1 or $Y^1$ or $Y^3$ replace a direct bond;

$R^4$ is hydrogen or $(C_1-C_4)$-alkyl;

m is 0, 1, 2, 3 or 4, preferably 1 or 2;

n is 0, 1, 2, 3 or 4, preferably 1 or 2;

Z is a direct bond, $NR^9$, O, $S(O)_s$ where s is 0, 1 or 2, $OSO_2$, $SO_2O$, $NR^{10}SO_2$, $SO_2NR^{11}$, $SiR^{12}R^{13}$, $U^1P(W^1)V^1V^2$ or

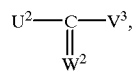

where $U^1$, $U^2$ independently of one another are a direct bond, $NR^{14}$ or O;

$W^1$, $W^2$ independently of one another are oxygen or sulfur, preferably oxygen;

$V^1$, $V^2$, $V^3$ are identical or different and are a direct bond, $NR^{15}$ or oxygen, where $R^9$, $R^{10}$, $R^{11}$, $R^{14}$ and $R^{15}$ are identical or different and are in each case hydrogen, alkyl, alkoxy, alkanoyl or cycloalkyl;

$R^5$ radicals are substituents which are independent of one another and are halogen, cyano, nitro, alkyl, alkenyl, alkynyl, cycloalkyl, cycloalkenyl and it being possible for one or more, preferably up to three, non-adjacent saturated carbon units in the last-mentioned 5 radicals to be replaced by a carbonyl group or by hetero atom units such as oxygen, $S(O)_x$ where x is 0, 1 or 2, $NR^{16}$ or $SiR^{17}R^{18}$, and it being possible for these last-mentioned 5 radicals, with or without the abovementioned variations, to be optionally substituted by one or more, preferably up to three, in the case of fluorine up to the maximum number of, identical or different radicals $D^1R^{19}$, or $R^5$ can be aryl or heterocyclyl, it being possible for these two radicals to be unsubstituted or to be substituted by up to three, in the case of fluorine also up to the maximum number of, identical or different radicals $D^2R^{20}$, or two adjacent radicals Z—$R^5$ together with the carbon atoms to which they are attached can form a fused cycle having 4 to 6 ring atoms which is carbocyclic or contains hetero ring atoms selected from the group consisting of O, S and N and which is unsubstituted or substituted by one or more radicals selected from the group consisting of halogen, $(C_1-C_4)$-alkyl and oxo, or $R^9$, $R^{10}$, $R^{11}$, $R^{14}$ or $R^{15}$ independently of one another together with the $R^5$ which is attached to Z can form a 4- to 8-membered ring system in which one or two $CH_2$ groups, preferably one $CH_2$ group, can be replaced by hetero atom units such as oxygen, $S(O)_t$ where t is 0, 1 or 2 or $NR^{25}$, where $R^6$ is hydrogen, $(C_1-C_4)$-alkyl, $(C_1-C_4)$-haloalkyl, $(C_2-C_4)$-alkenyl, $(C_2-C_4)$-haloalkenyl, $(C_2-C_4)$-alkynyl, $(C_2-C_4)$-haloalkynyl, $(C_1-C_4)$-alkoxy, $(C_1-C_4)$-haloalkoxy, $(C_1-C_4)$-alkylthio, $(C_1-C_4)$-haloalkylthio, $(C_1-C_4)$-alkanoyl, $(C_2-C_4)$-haloalkanoyl, $(C_3-C_5)$-cycloalkyl, $(C_1-C_4)$-alkylsulfonyl, $(C_1-C_4)$-haloalkylsulfonyl $(C_1-C_4)$-alkoxy-$(C_1-C_4)$-alkyl, $(C_1-C_4)$-alkoxycarbonyl;

$R^7$ and $R^8$ independently of one another are hydrogen, hydroxyl, halogen, cyano, $(C_1-C_4)$-alkyl, $(C_1-C_4)$-haloalkyl, $(C_2-C_4)$-alkenyl, $(C_2-C_4)$-haloalkenyl, $(C_2-C_4)$-alkynyl, $(C_2-C_4)$-haloalkenyl, $(C_3-C_5)$-cycloalkyl, $(C_1-C_4)$-alkanoyl, $(C_1-C_4)$-haloalkanoyl, $(C_1-C_4)$-alkoxy, $(C_1-C_4)$-haloalkoxy, $(C_1-C_4)$-alkylthio or $(C_1-C_4)$-haloalkylthio;

$R^{12}$ and $R^{13}$ independently of one another are $(C_1-C_4)$-alkyl or phenyl, preferably methyl;

$R^{16}$ is hydrogen, $(C_1-C_4)$-alkyl, $(C_1-C_4)$-alkoxy or $(C_1-C_4)$-alkanoyl;

$R^{17}$ and $R^{18}$ independently of one another are $(C_1-C_4)$-alkyl, preferably methyl;

$D^1$ and $D^2$ are in each case independent of one another and are a direct bond, oxygen, $S(O)_k$, $SO_2O$, $OSO_2$, $CO$, $OCO$, $COO$, $NR^{21}$, $SO_2NR^{21}$, $NR^{21}SO_2$, $ONR^{21}$, $NR^{21}O$, $NR^{21}CO$, $CONR^{21}$ or $SiR^{22}R^{23}$ and k is 0, 1 or 2, where $R^{21}$ radicals independently of one another are hydrogen, $(C_1-C_4)$-alkyl, $(C_1-C_4)$-alkanoyl or $(C_3-C_5)$-cycloalkyl;

$R^{22}$ and $R^{23}$ independently of one another are $(C_1-C_4)$-alkyl;

$R^{19}$ and $R^{20}$ independently of one another are hydrogen, cyano, nitro, halogen, alkyl, haloalkyl, alkenyl, haloalkenyl, alkynyl, haloalkynyl, alkoxyalkyl, haloalkoxyalkyl, alkylthioalkyl, haloalkylthioalkyl, cycloalkyl, cycloalkenyl, cycloalkylalkyl, cycloalkenylalkyl, aryl, heterocyclyl, arylalkyl or heterocyclylalkyl, it being possible for the cycloaliphatic, aromatic or heterocyclic ring systems in the last-mentioned 8 radicals to be unsubstituted or to be provided with up to three, in the case of fluorine also up to the maximum number of, identical or different substituents $R^{24}$, or $R^{19}$ and $R^{20}$, attached to the same carbon atom, together are an oxo group; where $R^{24}$ radicals independently of one another can be $(C_1-C_4)$-alkyl, $(C_1-C_4)$-haloalkyl, $(C_1-C_4)$-alkoxy, $(C_1-C_4)$-haloalkoxy, cyano, nitro or halogen;

$R^{25}$ independently of one another can be hydrogen, $(C_1-C_8)$-alkyl, $(C_1-C_4)$-haloalkyl, $(C_1-C_4)$-alkoxy, $(C_1-C_4)$-alkylthio, $(C_3-C_5)$-cycloalkyl, $(C_2-C_4)$-alkenyl, $(C_2-C_4)$-alkynyl, $(C_1-C_4)$-alkanoyl, $(C_1-C_4)$-haloalkanoyl, $(C_1-C_4)$-alkoxy-$(C_1-C_4)$-alkyl, phenyl-$(C_1-C_4)$-alkyl or phenyl, it being possible for the phenyl groups independently of one another to be unsubstituted or provided with up to three, in the case of fluorine also up to the maximum number of, identical or different substituents $R^{26}$, where $R^{26}$ substituents independently of one another can be $(C_1-C_4)$-alkyl, $(C_1-C_4)$-haloalkyl, $(C_1-C_4)$-alkoxy, $(C_1-C_4)$-alkylthio, halogen or cyano, and $R^{27}$ radicals independently of one another are $(C_1-C_4)$-alkyl, $(C_1-C_4)$-haloalkyl, preferably trifluoromethyl, halogen, $(C_1-C_4)$-alkoxy or $(C_1-C_4)$-haloalkoxy;

and salts thereof, preferably acid addition salts;

in particular those compound where $R^5$ radicals are substituents which are independent of one another and are halogen, cyano, nitro, $(C_1-C_{20})$-alkyl, $(C_2-C_{20})$-alkenyl, $(C_2-C_{20})$-alkynyl, $(C_3-C_8)$-cycloalkyl, $(C_4-C_8)$-cycloalkenyl and one or more, preferably up to three, non-adjacent saturated carbon units in the last-mentioned 5 radicals can be replaced by a carbonyl group or by hetero atom units such as oxygen, $S(O)_x$ where x is 0, 1 or 2, $NR^{16}$ or $SiR^{17}R^{18}$ and it being possible for these last-mentioned 5 radicals, with or without the abovementioned variations, to be optionally substituted by one or more, preferably up to three, in the case of fluorine up to the maximum number of, identical or different radicals $D^1R^{19}$, or $R^5$ can be aryl or heterocyclyl, it being possible for these two radicals to be unsubstituted or to be substituted by up to three, in the case of fluorine also up to the maximum number of, identical or different radicals $D^2R^{20}$, or two adjacent radicals Z—$R^5$ together with the carbon atoms to which they are attached can form a fused cycle having 4 to 6 ring atoms which is carbocyclic or contains hetero ring atoms selected from the group consisting of O, S and N and which is unsubstituted or substituted by one or more radicals selected from the group consisting of halogen, $(C_1-C_4)$-alkyl and oxo, or $R^9$, $R^{11}$ or $R^{15}$ independently of one another together with the $R^5$ attached to Z can form a 4- to 8-membered ring system in which one or two $CH_2$ groups, preferably one $CH_2$ group, can be replaced by hetero atom units such as oxygen, $S(O)_t$ where t is 0, 1 or 2 or $NR^{25}$, where $R^{16}$ is hydrogen, $(C_1-C_4)$-alkyl, $(C_1-C_4)$-alkoxy or $(C_1-C_4)$-alkanoyl;

$R^{17}$ and $R^{18}$ independently of one another are $(C_1-C_4)$-alkyl, preferably methyl; $D^1$ and $D^2$ are in each case independent of one another and are a direct bond, oxygen, $S(O)_k$, $SO_2O$, $OSO_2$, $CO$, $OCO$, $COO$, $NR^{21}$, $SO_2NR^{21}$, $NR^{21}SO_2$, $ONR^{21}$, $NR^{21}O$, $NR^{21}CO$, $CONR^{21}$ or $SiR^{22}R^{23}$ and k is 0, 1 or 2, where $R^{21}$ radicals independently of one another are hydrogen, $(C_1-C_4)$-alkyl, $(C_1-C_4)$-alkanoyl or $(C_3-C_5)$-cycloalkyl;

$R^{22}$ and $R^{23}$ independently of one another are $(C_1-C_4)$-alkyl;

$R^{19}$ and $R^{20}$ independently of one another are hydrogen, cyano, nitro, halogen, $(C_1-C_8)$-alkyl, $(C_1-C_8)$-haloalkyl, $(C_2-C_8)$-alkenyl, $(C_2-C_8)$-haloalkenyl, $(C_2-C_8)$-alkynyl, $(C_2-C_8)$-haloalkynyl, $(C_1-C_8)$-alkoxy-$(C_1-C_4)$-alkyl, $(C_1-C_8)$-haloalkoxy-$(C_1-C_4)$-alkyl, $(C_1-C_8)$-alkylthio-$(C_1-C_4)$-alkyl, $(C_1-C_8)$-haloalkylthio-$(C_1-C_4)$-alkyl, $(C_3-C_8)$-cycloalkyl, $(C_4-C_8)$-cycloalkenyl, $(C_3-C_8)$-cycloalkyl-$(C_1-C_4)$-alkyl, $(C_4-C_8)$-cycloalkenyl-$(C_1-C_4)$-alkyl, aryl, heterocyclyl, aryl-$(C_1-C_4)$-alkyl or heterocyclyl-$(C_1-C_4)$-alkyl, where, in the last-mentioned 8 radicals, the cycloaliphatic, aromatic or heterocyclic ring systems can be unsubstituted or provided with up to three, in the case of fluorine also up to the maximum number of, identical or different substituents $R^{24}$, or $R^{19}$ and $R^{20}$, attached to the same carbon atom, together are an oxo group, where $R^{24}$ can be $(C_1-C_4)$-alkyl, $(C_1-C_4)$-haloalkyl, $(C_1-C_4)$-alkoxy, $(C_1-C_4)$-haloalkoxy, cyano, nitro or halogen;

$R^{25}$ radicals are hydrogen, $(C_1-C_8)$-alkyl, $(C_1-C_4)$-haloalkyl, $(C_1-C_4)$-alkoxy, $(C_1-C_4)$-alkylthio, $(C_3-C_5)$-cycloalkyl, $(C_2-C_4)$-alkenyl, $(C_2-C_4)$-alkynyl, $(C_1-C_4)$-alkanoyl, $(C_2-C_4)$-haloalkanoyl, $(C_2-C_4)$-alkoxyalkyl, phenyl-$(C_1-C_4)$-alkyl or phenyl and the phenyl groups can be unsubstituted or provided with up to three, in the case of fluorine also up to the maximum number of, identical or different substituents $R^{26}$, where $R^{26}$ can be $(C_1-C_4)$-alkyl, $(C_1-C_4)$-haloalkyl, $(C_1-C_4)$-alkoxy, $(C_1-C_4)$-alkylthio, halogen or cyano.

Preferred compounds of the formula I are those in which $R^1$ is hydrogen, chlorine or fluorine;

$R^2$ is $(C_1-C_4)$-alkyl, $(C_2-C_4)$-alkenyl, $(C_2-C_4)$-alkynyl, tri-$(C_1-C_4)$-alkylsilyl-$(C_2-C_4)$-alkynyl, $(C_1-C_4)$-haloalkyl, cyclopropyl, halocyclopropyl, methoxymethyl or cyano;

$R^3$ is hydrogen, halogen, methyl, ethyl, ethenyl, ethynyl, methoxy, ethoxy, cyano, trifluoromethyl, fluoromethylthio or methoxycarbonyl; or $R^2$ and $R^3$ together with the carbon atoms to which they are bonded form an optionally substituted unsaturated 5- or 6-membered ring which, in the case of a 5-membered ring, can contain a sulfur atom instead of a $CH_2$ unit; or $R^2$ and $R^3$ together with the carbon atoms to which they are bonded form a saturated 5- or 6-membered ring which can contain a sulfur or an oxygen atom instead of a $CH_2$ unit;

A is CH or N;

X is NH or oxygen;

$Y^1$, $Y^2$ and $Y^3$ independently of one another are a group of the formula —O—, —S(O)$_r$—, —N(O)$_l R^6$— or $CR^7R^8$ where r is =0, 1 or 2 and l is 0 or 1; or $Y^1$ or $Y^2$ replace a direct bond;

$R_4$ is hydrogen;

m is 1 or 2;

n is 1 or 2;

Z is a direct bond, $NR^9$, O, $S(O)_s$ where s is 0, 1 or 2, or $OSO_2$, $SO_2O$, $NR^{10}SO_2$, $SO_2NR^{11}$, $SiR^{12}R^{13}$, $U^1P(W^1)V^1V^2$ or

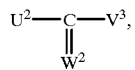

where $U^1$, $U^2$ independently of one another are a direct bond, $NR^{14}$ or O;

$W^1$, $W^2$ are oxygen;

$V^1$, $V^2$, $V^3$ independently of one another are a direct bond, $NR^{15}$ or oxygen; where $R^6$ radicals independently of one another can be $(C_1-C_4)$-alkyl or $(C_1-C_4)$-alkanoyl;

$R^7$ and $R^8$ independently of one another are hydrogen, halogen or $(C_1-C_4)$-alkyl, and $R^9$, $R^{10}$, $R^{11}$, $R^{14}$ and $R^{15}$ are identical or different and are in each case hydrogen, $(C_1-C_4)$-alkyl, $(C_1-C_4)$-alkoxy, $(C_1-C_4)$-alkanoyl or $(C_3-C_5)$-cycloalkyl;

in particular those compounds in which $R^1$ is hydrogen or fluorine;

$R^2$ is methyl, ethyl, propyl, isopropyl, $(C_1-C_2)$-fluoroalkyl or methoxymethyl;

$R^3$ is halogen, methyl, ethyl, ethenyl, ethynyl, methoxy, ethoxy, trifluoromethyl, fluoromethylthio, methoxycarbonyl or cyano; or $R^2$ and $R^3$ together with the ring system to which they are bonded form the quinazoline or quinoline system, which can be substituted in the carbocyclic moiety by fluorine; or $R^2$ and $R^3$ together with the carbon atoms to which they are bonded form a saturated 6-membered ring which can contain an oxygen or sulfur atom instead of a $CH_2$ group;

A is CH or N;

X is NH or oxygen;

$Y^1$, $Y^2$ and $Y^3$ are a group of the formula —O—, or —S(O)$_r$—, where r is 0, 1 or 2, or a group of the formula $CR^7R^8$, or $Y^1$ or $Y^3$ replace a direct bond, where $R^7$ and $R^8$ independently of one another are hydrogen or methyl.

Especially preferred are those compounds of the formula I in which $R^1$ is hydrogen;

$R^2$ is ethyl, propyl, isopropyl, 1-fluoroethyl or methoxymethyl;

$R^3$ is fluorine, chlorine, bromine, cyano, methoxy, ethenyl or ethynyl; or, in the event that A is nitrogen, $R^2$ and $R^3$ together with the ring system to which they are bonded form the quinazoline system which can be substituted by a fluorine atom.

Most preferred are those compounds of the formula I where $R^1$ is hydrogen;

$R^2$ is ethyl or methoxymethyl;

$R^3$ is fluorine, chlorine, bromine or methoxy;

$R^5$ radicals are substituents which are independent of one another and are halogen, cyano, nitro, $(C_1-C_8)$-alkyl, $(C_2-C_8)$-alkenyl, $(C_2-C_8)$-alkynyl, $(C_3-C_8)$-cycloalkyl, $(C_4-C_8)$-cycloalkenyl and it is possible for one or more, preferably up to three, non-adjacent saturated carbon units in the last-mentioned 5 radicals to be replaced by a carbonyl group or by hetero atom units such as oxygen, $S(O)_x$ where x is 0, 1 or 2, $NR^{16}$ or $SiR^{17}R^{18}$, and these last-mentioned 5 radicals, with or without the abovementioned variations, can be optionally substituted by one or more, preferably up to three, in the case of fluorine up to the maximum number of, identical or different radicals $D^1R^{19}$, or $R^5$ can be aryl or heterocyclyl, it being possible for these two radicals to be unsubstituted or to be substituted by up to three, in the case of fluorine also up to the maximum number of, identical or different radicals $D^2R^{20}$, or two adjacent radicals Z—$R^5$ together with the carbon atoms to which they are attached can form a fused cycle having 4 to 6 ring atoms which is carbocyclic or contains hetero ring atoms selected from the group consisting of O, S and N and which is unsubstituted or substituted by one or more radicals selected from the group consisting of halogen, $(C_1-C_4)$-alkyl and oxo, or $R^{11}$ or $R^{15}$ independently of one another together with the $R^5$ which is attached to Z can form a 4- to 8-membered ring system in which one or two $CH_2$ groups, preferably one $CH_2$ group, can be replaced by hetero atom units such as oxygen, $S(O)_t$ where t is 0, 1 or 2 or $NR^{25}$, where $R^{16}$ radicals independently of one another are hydrogen, $(C_1-C_4)$-alkyl, $(C_1-C_4)$-alkoxy or $(C_1-C_4)$-alkanoyl, and $R^{17}$ and $R^{18}$ independently of one another are $(C_1-C_4)$-alkyl, preferably methyl;

$D^1$ and $D^2$ are in each case independent of one another and are a direct bond, —O—, —S(O)$_k$—, —SO$_2$O—, —OSO$_2$—, —CO—, —OCO—, —COO—, —NR$^{21}$—, —SO$_2$NR$^{21}$—, —NR$^{21}$SO$_2$—, —ONR$^{21}$—, —NR$^{21}$O—, —NR$^{21}$CO—, —CONR$^{21}$—, and k is =0, 1 or 2, and where $R^{21}$ radicals independently of one another are hydrogen, $(C_1-C_4)$-alkyl, $(C_1-C_4)$-alkanoyl or $(C_3-C_5)$-cycloalkyl;

$R^{19}$ and $R^{20}$ independently of one another are hydrogen, halogen, preferably fluorine, $(C_1-C_8)$-alkyl, $(C_3-C_8)$-cycloalkyl, aryl or heterocyclyl, it being possible for the cycloaliphatic, aromatic or heterocyclic ring systems in the last-mentioned three radicals to be unsubstituted or provided with up to three, in the case of fluorine also up to the maximum number of, identical or different substituents $R^{24}$, where $R^{24}$ radicals independently of one another can be $(C_1-C_4)$-alkyl, $(C_1-C_4)$-haloalkyl, $(C_1-C_4)$-alkoxy, $(C_1-C_4)$-haloalkoxy, cyano, nitro, halogen;

$R^{25}$ radicals independently of one another are $(C_1-C_8)$-alkyl, $(C_3-C_5)$-cycloalkyl, $(C_1-C_4)$-alkanoyl, $(C_2-C_4)$-haloalkanoyl, $(C_1-C_4)$-alkoxy-$(C_1-C_4)$-alkyl, phenyl-$(C_1-C_4)$-alkyl or phenyl and the phenyl groups can be unsubstituted or provided with up to three, in the case of fluorine also up to the maximum number of, identical or different substituents $R^{26}$, where $R^{26}$ radicals independently of one another can be $(C_1-C_4)$-alkyl, $(C_1-C_4)$-haloalkyl, $(C_1-C_4)$-alkoxy, $(C_1-C_4)$-alkylthio, halogen or cyano;

in particular those compounds where $R^5$ radicals independently of one another are $(C_1-C_8)$-alkyl in which one or more, preferably up to three, non-adjacent saturated carbon units can be replaced by oxygen and which, with or without the abovementioned variations, can optionally be substituted by one or more, preferably up to three, in the case of fluorine up to the maximum number of, identical or different radicals $D^1R^{19}$, or $R^5$ can be aryl or heterocyclyl, it being possible for these two radicals to be unsubstituted or substituted by up to three, in the case of fluorine also up to the maximum number of, identical or different radicals $D^2R^{20}$.

In the above formula, "halogen" is to be understood as meaning a fluorine, chlorine, bromine or iodine atom;

the term "$(C_1-C_4)$-alkyl" is to be understood as meaning an unbranched or branched hydrocarbon radical having 1 to 4 carbon atoms such as, for example, the methyl, ethyl, propyl, isopropyl, 1-butyl, 2-butyl, 2-methylpropyl or tert-butyl radical;

the term "$(C_1-C_8)$-alkyl" the abovementioned alkyl radicals and also, for example, the pentyl, 2-methylbutyl, 1,1-dimethylpropyl, hexyl, heptyl, octyl, or 1,1,3,3-tetramethylbutyl radical;

the term "$(C_1-C_{20})$-alkyl" the abovementioned alkyl radicals and also, for example, the dodecyl, pentadecyl or eicosyl radical;

the term "$(C_1-C_4)$-haloalkyl" an alkyl group mentioned under the term "$(C_1-C_4)$-alkyl" in which one or more hydrogen atoms are replaced by the abovementioned halogen atoms, preferably chlorine and fluorine, such as, for example, the trifluoromethyl, 1-fluoroethyl, 2-fluoroethyl, 2,2,2-trifluoroethyl, chloromethyl, fluoromethyl, difluoromethyl or the 1,1,2,2-tetrafluoroethyl group;

the term "$(C_1-C_2)$-fluoroalkyl", for example, the mono-, di-, trifluoromethyl, 1-fluoroethyl, 2-fluoroethyl, 2,2-difluoroethyl, 1,1-difluoroethyl or the 2,2,2-trifluoroethyl group;

the term "cycloalkyl" preferably $(C_3-C_8)$-cycloalkyl;

the term "cycloalkenyl" preferably $(C_3-C_8)$-cycloalkenyl;

the term "$(C_3-C_5)$-cycloalkyl" the cyclopropyl, cyclobutyl or cyclopentyl group;

the term "$(C_3-C_8)$-cycloalkyl" the radicals mentioned above under "$(C_3-C_5)$-cycloalkyl" and also the cyclohexyl, cycloheptyl or cyclooctyl radical, but also bicyclic systems such as, for example, the norbornyl group or the bicyclo[2.2.2]octane radical;

the term "$(C_3-C_5)$-halocycloalkyl" one of the above-listed $(C_3-C_5)$-cycloalkyl radicals in which one or more, in the case of fluorine optionally also all, hydrogen atoms are replaced by halogen, preferably fluorine or chlorine, such as, for example, the 2,2-difluoro- or 2,2-dichlorocyclopropane group or the fluorocyclopentane radical;

the term "$(C_2-C_4)$-alkenyl" for example the vinyl, allyl, 2-methyl-2-propenyl or 2-butenyl group;

the term "$(C_2-C_8)$-alkenyl" the radicals mentioned above under "$(C_2-C_4)$-alkenyl" and, for example, the 2-pentenyl or the 2-octenyl group;

the term "$(C_2-C_{20})$-alkenyl" the radicals mentioned above under "$(C_2-C_8)$-alkenyl" and also, for example, the 2-decenyl or the 2-eicosenyl group;

the term "$(C_2-C_4)$-haloalkenyl" a $(C_2-C_4)$-alkenyl group in which some or else, in the case of fluorine, all hydrogen atoms are replaced by halogen, preferably fluorine or chlorine, the term "$(C_2-C_8)$-haloalkyl" a $(C_2-C_8)$-alkenyl group in which some, in the case of fluorine also all, hydrogen atoms are replaced by halogen, preferably fluorine or chlorine;

the term "$(C_4-C_5)$-cycloalkenyl" the cyclobutenyl or cyclopentenyl group;

the term "$(C_4-C_8)$-cycloalkenyl" the abovementioned radicals and also, for example, the 1-cyclohexenyl group;

the term "$(C_2-C_4)$-alkynyl", for example, the ethynyl, propargyl, 2-methyl-2-propynyl, 1-butynyl, 2-butynyl or the 3-butynyl group;

the term "$(C_2-C_8)$-alkynyl" the radicals mentioned above under "$(C_2-C_4)$-alkynyl" and also, for example, the 2-pentynyl or the 2-octynyl group, the term "$(C_2-C_{20})$-alkynyl" the radicals mentioned above under "$(C2-C_8)$-alkynyl" and also, for example, the 2-decynyl group;

the term "$(C_2-C_4)$-haloalkynyl" a $(C_2-C_4)$-alkynyl group in which some, in the case of fluorine also all, hydrogen atoms are replaced by halogen atoms, preferably fluorine or chlorine, or else the iodoethynyl group;

the term "$(C_2-C_8)$-haloalkynyl" a $(C_2-C_8)$-alkynyl group in which some, in the case of fluorine all, hydrogen atoms are replaced by halogen atoms, preferably fluorine or chlorine;

the term "tri-($C_1$–$C_4$)-alkylsilyl-($C_2$–$C_4$)-alkynyl" preferably the trimethylsilylethynyl group;

the term "($C_1$–$C_4$)-hydroxyalkyl" for example the hydroxymethyl, 1-hydroxyethyl, 2-hydroxyethyl, 1-hydroxy-1-methylethyl or the 1-hydroxypropyl group;

the term "($C_1$–$C_4$)-alkanoyl" for example the formyl, acetyl, propionyl, 2-methylpropionyl or butyryl group;

the term "($C_2$–$C_4$)-haloalkanoyl" a ($C_2$–$C_4$)-alkanoyl group in which some, in the case of fluorine all, hydrogen atoms are replaced by halogen atoms, preferably fluorine or chlorine;

the term "cyano-($C_1$–$C_4$)-alkyl" a cyanoalkyl group whose hydrocarbon radical has the meaning given under the term "($C_1$–$C_4$)-alkyl";

the term "($C_1$–$C_4$)-alkoxycarbonyl" for example the methoxycarbonyl, ethoxycarbony, propoxycarbonyl, butoxycarbonyl or tert-butoxycarbonyl group;

the term "($C_1$–$C_4$)-haloalkoxycarbonyl" a ($C_1$–$C_4$)-alkoxycarbonyl group in which one or more, in the case of fluorine all, hydrogen atoms are replaced by halogen, preferably fluorine or chlorine;

the term "($C_1$–$C_4$)-alkylthio" an alkylthio group whose hydrocarbon radical has the meaning given under the term "($C_1$–$C_4$)-alkyl";

the term "($C_1$–$C_4$)-haloalkylthio" a ($C_1$–$C_4$)-alkylthio group in which one or more, in the case of fluorine optionally also all, hydrogen atoms of the hydrocarbon radical are replaced by halogen, preferably chlorine or fluorine;

the term "fluoromethylthio" the mono-, di- and trifluoromethylthio group;

the term "($C_1$–$C_4$)-alkylsulfinyl" for example the methyl-, ethyl-, propyl-, isopropyl-, butyl-, isobutyl-, sec-butyl- or tert-butylsulfinyl group;

the term "($C_1$–$C_4$)-alkylsulfonyl" for example the methyl-, ethyl-, propyl-, isopropyl-, butyl-, isobutyl-, sec-butyl- or tert-butylsulfonyl group;

the terms "($C_1$–$C_4$)-haloalkylsulfinyl" and "($C_1$–$C_4$)-haloalkylsulfonyl" ($C_1$–$C_4$)-alkylsulfinyl- and -sulfonyl radicals having the meanings given above in which one or more, in the case of fluorine optionally also all, hydrogen atoms of the hydrocarbon radical are replaced by halogen, preferably chlorine or fluorine;

the term "($C_1$–$C_4$)-alkoxy" an alkoxy group whose hydrocarbon radical has the meaning given under the term "($C_1$–$C_4$)-alkyl";

the term "($C_1$–$C_4$)-haloalkoxy" a haloalkoxy group whose halohydrocarbon radical has the meaning given under the term "($C_1$–$C_4$)-haloalkyl";

the term "($C_1$–$C_4$)-alkoxy-($C_1$–$C_4$)-alkyl" for example the 1-methoxyethyl, 2-methoxyethyl, 2-ethoxyethyl, methoxymethyl, ethoxymethyl, 3-methoxypropyl or the 4-butoxybutyl group;

the terms "($C_1$–$C_4$)-haloalkoxy-($C_1$–$C_4$)-alkyl", "($C_1$–$C_4$)-alkoxy-($C_1$–$C_4$)-haloalkyl" and "($C_1$–$C_4$)-haloalkoxy-($C_1$–$C_4$)-haloalkyl" ($C_1$–$C_4$)-alkoxy-($C_1$–$C_4$)-alkyl radicals having the meanings given above in which one or more, in the case of fluorine optionally also all, hydrogen atoms in the relevant hydrocarbon moieties are replaced by halogen, preferably chlorine or fluorine;

the term "($C_1$–$C_4$)-alkylthio-($C_1$–$C_4$)-alkyl" for example methylthiomethyl, ethylthiomethyl, propylthiomethyl, 2-methylthioethyl, 2-ethylthioethyl or 3-methylthiopropyl;

the term "($C_3$–$C_5$)-cycloalkoxy" the cyclopropoxy, cyclobutoxy or cyclopentoxy group;

the term "($C_3$–$C_8$)-cycloalkyl-($C_1$–$C_4$)-alkyl" for example a cyclopropylmethyl, a cyclopentylethyl or a cyclohexylmethyl group;

the term "($C_4$–$C_8$)-cycloalkenyl-($C_1$–$C_4$)-alkyl" for example a cyclobutenylmethyl group, a cyclopenten-1-ylethyl group or a cyclohexene-3-ylmethyl group;

the term "phenyl-($C_1$–$C_4$)-alkyl" preferably benzyl;

the term "aryl-($C_1$–$C_4$)-alkyl" for example the benzyl, the 2-phenylethyl, the 1-phenylethyl, the 1-methyl-1-phenylethyl group, the 2-phenylpropyl, the 4-phenylbutyl group, the 2-methyl-2-phenylethyl group or the 1-methyl- or 2-methylnaphthyl group;

the term "heterocyclyl-($C_1$–$C_4$)-alkyl" for example the thienylmethyl, pyridylmethyl, furfuryl-, tetrahydrofurfuryl-, tetrahydropyranylmethyl or the 1,3-dioxolan-2-ylmethyl group;

the term "aryl" a carbocyclic aromatic radical having preferably 6 to 14, in particular 6 to 12, carbon atoms such as, for example, phenyl, naphthyl or biphenyl, preferably phenyl;

the term "heterocyclyl" a heteroaromatic or heteroaliphatic ring system, "heteroaromatic ring system" to be understood as meaning an aryl radical in which at least one CH group is replaced by N and/or at least two adjacent CH groups are replaced by S, NH or O, for example a radical of thiophene, furan, pyrrole, thiazole, oxazole, imidazole, isothiazole, isoxazole, pyrazole, 1,3,4-oxadiazole, 1,3,4-thiadiazole, 1,3,4-triazole, 1,2,4-oxadiazole, 1,2,4-thiadiazole, 1,2,4-triazole, 1,2,3-triazole, 1,2,3,4-tetrazole, benzo[b]thiophene, benzo[b]furan, indole, benzo[c]thiophene, benzo[c]furan, isoindole, benzoxazole, benzothiazole, benzimidazole, benzisoxazole, benzisothiazole, benzopyrazole, benzothiadiazole, benzotriazole, dibenzofuran, dibenzothiophene, carbazole, pyridine, pyrazine, pyrimidine, pyridazine, 1,3,5-triazine, 1,2,4-triazine, 1,2,4,5-triazine, quinoline, isoquinoline, quinoxaline, quinazoline, cinnoline, 1,8-naphthyridine, 1,5-naphthyridine, 1,6-naphthyridine, 1,7-naphthyridine, phthalazine, pyridopyrimidine, purine, pteridine or 4H-quinolizine;

and the term "heteroaliphatic ring system" a ($C_3$–$C_8$)-cycloalkyl radical in which at least one carbon unit is replaced by O, S or a group $NR^{11}$ and $R^{11}$ is hydrogen, ($C_1$–$C_4$)-alkyl, ($C_1$–$C_4$)-alkoxy or aryl.

What has been explained above applies analogously to homologs or radicals derived therefrom.

The present invention relates to the compounds of the formula I in the form of the free bases or of a salt, preferably an acid addition salt. Acids which can be used for salt formation are, for example, inorganic acids such as hydrochloric acid, hydrobromic acid, nitric acid, sulfuric acid, phosphoric acid, or organic acids such as formic acid, acetic acid, propionic acid, malonic acid, oxalic acid, fumaric acid, adipic acid, stearic acid, oleic acid, methanesulfonic acid, benzenesulfonic acid or toluenesulfonic acid.

Some of the compounds of the formula I have one or more asymmetric carbon atoms or stereoisomers on double bonds. Enantiomers or diastereomers are therefore possible. The scope of the invention extends both to the pure isomers and also to mixtures of these. The diastereomer mixtures can be separated into the components by customary methods, for example by selective crystallization from suitable solvents or by chromatography. Racemates can be resolved by customary methods to give the enantiomers, for example by salt formation with an optically active acid, separation of the diastereomeric salts and liberation of the pure enantiomers by means of a base.

The invention furthermore relates to a process for the preparation of compounds of the formula I which comprises reacting a compound of the formula II

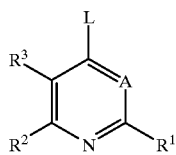

(II)

where A, $R^1$, $R^2$ and $R^3$ have the meanings given above for formula I and L is a leaving group, for example halogen, alkylthio, alkanesulfonyloxy or arylsulfonyloxy, alkylsulfonyl or arylsulfonyl, with a nucleophile of the formula III

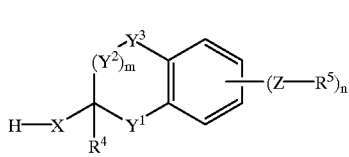

(III)

where X, $Y^1$, $Y^2$, $Y^3$, Z, $R^4$, $R^5$, m and n have the meanings given above for formula I and, if appropriate, further derivatizing the nitrogen heterocycle or the side chain(s) $R^5$ in the compounds of the formula I obtained in this or another manner.

The above-described substitution reaction is known in principle. The leaving group L can be varied within wide limits and can be, for example, a halogen atom such as fluorine, chlorine, bromine or iodine, or alkylthio such as methyl- or ethylthio, or alkanesulfonyloxy such as methane-, trifluoromethane- or ethanesulfonyloxy or arylsulfonyloxy, such as benzenesulfonyloxy or toluenesulfonyloxy, or alkylsulfonyl such as methyl- or ethylsulfonyl, or arylsulfonyl such as phenyl- or toluenesulfonyl.

The abovementioned reaction is carried out in a temperature range of from 20 to 150° C., expediently in the presence of a base and, if appropriate, in an inert organic solvent such as, for example, N,N-dimethylformamide, N,N-dimethylacetamide, dimethyl sulfoxide, N-methylpyrrolidin-2-one, dioxane, tetrahydrofuran, 4-methyl-2-pentanone, methanol, ethanol, butanol, ethylene glycol, ethylene glycol dimethyl ether, toluene, chlorobenzene or xylene. Mixtures of the abovementioned solvents can also be used.

In the event that X is oxygen, examples of suitable bases are alkali metal carbonates, alkali metal hydrogen carbonates, alkali metal amides, alkali metal hydrides, alkaline earth metal carbonates, alkaline earth metal hydrogen carbonates, alkaline earth metal amides or alkaline earth metal hydrides such as sodium carbonate, sodium hydrogen carbonate, potassium carbonate, sodium amide or sodium hydride, and in the event that X is NH, examples of suitable bases are alkali metal carbonates, alkali metal hydrogen carbonates, alkali metal hydroxides, alkali metal amides, alkali metal hydrides, alkaline earth metal carbonates, alkaline earth metal hydrogen carbonates, alkaline earth metal hydroxides, alkaline earth metal amides or alkaline earth metal hydrides such as sodium carbonate, sodium hydrogen carbonate, potassium carbonate, sodium hydroxide, sodium amide or sodium hydride or organic bases such as triethylamine or pyridine. A second equivalent of an amine of the formula III can also be employed as auxiliary base.

Most of the compounds of the formula II which are required as starting materials are known from the literature or can be prepared analogously to known methods (cf. EP 370 391, EP 470 600, DOS 43 31 179, DOS 44 04 702).

To prepare the nucleophiles of the formula III, suitably substituted ketones of the formula IV are used as starting materials and are converted into the corresponding amines by reductive amination ($H_2$, $NH_3$, metal catalyst or ammonium acetate/sodium cyanoborohydride or Leuckart-Wallach reduction) or into the corresponding alcohols by reduction with a complex metal hydride.

Furthermore, the nucleophiles of the formula III where X=NH can be prepared by reducing an oxime or imine or by subjecting an alkyl halide or alkyl tosylate to a Gabriel reaction or to a Mitsunobu reaction with phthalimide and subsequent hydrazinolysis. Equally, these nucleophiles can be synthesized by reacting an alkyl halide or alkyl tosylate with a metal azide and reducing the azide with a suitable reducing agent, for example a complex metal hydride, hydrogen in the presence of a hydrogenation catalyst or phosphine or phosphite. Regarding the preparation of the 2-aminoindenes, the following synthesis route is also possible: D. E. Nichols, W. K. Brewster, M. P. Johnson, R. Overlender and R. U. Riggs, J. Med. Chem. 1990, 33, 703. 2-Aminochromanes are also obtainable via other routes (cf. WO 90/12795).

The ketones of the formula IV

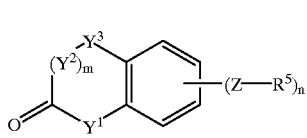

(IV)

are commercially available, known from the literature or can be synthesized analogously to known processes:

J. J. Sims, L. H. Selman, M. Cadogan, Org. Synth. 1971, 61,109;

S. Lee, S. P. Frescas, O. E. Nichols, Synth. Commun. 1995, 2775;

G. D. Johnson, Org. Synth. 1963, IV, 900;

D. Hackle, I. M. Lockhardt, M. Wright, J. Med. Chem. 1969, 12, 277;

R. J. Heffner, M. M. Joullie, Synth. Commun. 1991, 2231; Krollpfeiffer, Schulze, Chem. Ber. 1923, 56, 1822.

The active substances are well tolerated by plants and have a favorable toxicity to warm-blooded species and are suitable for controlling animal pests, in particular insects, arachnids, helminths and molluscs and their eggs, very especially preferably for controlling insects and arachnids found in agriculture, in livestock breeding, in forests, in the protection of stored products and materials and in the hygiene sector. They are effective against normally sensitive and resistant species and all or some developmental stages. The abovementioned pests include:

From the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp., Tetranychus spp., Eotetranychus spp., Oligonychus spp., Eutetranychus spp.

From the order of the Isopoda, for example, *Oniscus asselus, Armadium vulgar, Porcellio scaber.*

From the order of the Diplopoda, for example, *Blaniulus guttulatus.*

From the order of the Chilopoda, for example, *Geophilus carpophagus,* Scutigera spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea madeirae, Blatella germanica, Acheta domesticus,* Gryllotalpa spp., *Locusta migratoria migratorioides, Melanoplus differentialis, Schistocerca gregaria.*

From the order of the Isoptera, for example, Reticulitermes spp.

From the order of the Anoplura, for example, *Phylloxera vastatrix,* Pemphigus spp., Pediculus humanus corporis, Haematopinus spp., Linognathus spp.

From the order of the Mallophaga, for example, Trichodectes pp., Damalinea spp.

From the order of the Thysanoptera, for example, *Hercinothrips femoralis, Thrips tabaci.*

From the order of the Heteroptera, for example, Eurygaster spp., *Dysdercus intermedius, Piesma quadrata, Cimex lectularius, Rhodnius prolixus,* Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelus bilobatus, Nephotettix cincticeps, Lecanium corni, Saissetia oleae, Laodelphax striatellus, Nilaparvata lugens, Aonidiella aurantii, Aspidiotus hederae,* Pseudococcus spp., Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima, Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylloides chrysocephala, Epilachna varivestis,* Atomaria spp., *Oryzaephilus surinamensis,* Anthonumus spp., Sitophilus spp., *Otiorrhynchus sulcatus, Cosmopolites sordidus, Ceuthorrynchus assimilis, Hypera postica,* Dermestes spp., Trogoderma, Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis, Costelytra zealandica.*

From the order of the Hymenoptera, for example, Diprion spp., Hoplocampa spp., Lasius spp., *Monomorium pharaonis,* Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hypobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae, Tipula paludosa.*

From the order of the Siphonaptera, for example, *Xenopsylla cheopsis,* Ceratophyllus spp.

From the order of the Arachnida, for example, *Scorpio maurus, Latrodectus mactans.*

From the class of the helminths, for example, Haemonchus, Trichostrongulus, Ostertagia, Cooperia, Chabertia, Strongyloides, Oesophagostomum, Hyostrongulus, Ancylostoma, Ascaris and Heterakis and also Fasciola.

From the class of the gastropods, for example, Deroceras spp., Arion spp., Lymnaea spp., Galba spp., Succinea spp., Biomphalaria spp., Bulinus spp., Oncomelania spp.

From the class of the bivalves, for example, Dreissena spp.

The plant-parasitic nematodes which can be controlled according to the invention include, for example, the root-parasitic soil nematodes such as, for example, those from the genera Meloidogyne (root-knot nematodes, such as *Meloidogyne incognita, Meloidogyne hapla* and *Meloidogyne javanica*), Heterodera and Globodera (cyst-forming nematodes, such as *Globodera rostochiensis, Globodera pallida, Heterodera trifolii*) and from the genera Radopholus, such as *Radopholus similis,* Pratylenchus, such as *Pratylenchus neglectus, Pratylenchus penetrans* and *Pratylenchus curvitatus;* Tylenchulus, such as *Tylenchulus semipenetrans,* Tylenchorhynchus, such as *Tylenchorhynchus dubius* and *Tylenchorhynchus claytoni,* Rotylenchus, such as *Rotylenchus robustus,* Heliocotylenchus, such as *Haliocotylenchus multicinctus,* Belonoaimus, such as *Belonoaimus longicaudatus,* Longidorus, such as *Longidorus elongatus,* Trichodorus, such as *Trichodorus primitivus* and Xiphinema, such as Xiphinema index.

Furthermore, the compounds according to the invention can be used for controlling the nematode genera Ditylenchus (stem parasites, such as *Ditylenchus dipsaci* and *Ditylenchus destructor*), Aphelenchoides (foliar nematodes, such as *Aphelenchoides ritzemabosi*) and Anguina (flower and leaf-gall nematodes, such as *Anguina tritici*).

The invention also relates to compositions, in particular to insecticidal, acaricidal and ovicidal compositions, which comprise the compounds of the formula I in addition to suitable formulation auxiliaries.

The compositions according to the invention comprise the active ingredients of the formula I in a concentration range of from 0.00000001 to 95% by weight, preferably from 1 to 95% by weight.

They can be formulated in various ways, depending on the prevailing biological and/or chemico-physical parameters. The following formulations are therefore possible:

Wettable powders (WP), emulsifiable concentrates (EC), aqueous solutions (SL), emulsions, sprayable solutions, oil- or water-based dispersions (SC), suspoemulsions (SE), dusts (DP), seed-treatment products, granules in the form of microgranules, spray granules, coated granules and adsorption granules, water-dispersible granules (WG), ULV formulations, microcapsules, waxes or baits.

These individual types of formulation are known in principle and are described, for example, in:

Winnacker-Küchler, "Chemische Technologie" [Chemical Engineering], Volume 7, C. Hauser Verlag Munich, 4th Ed. 1986; van Falkenberg, "Pesticides Formulations", Marcel Dekker N.Y., 2nd Ed. 1972–73; K. Martens, "Spray Drying Handbook", 3rd Ed. 1979, G. Goodwin Ltd. London.

The formulation auxiliaries required, such as inert materials, surfactants, solvents and other additives are also known and are described, for example, in:

Watkins, "Handbook of Insecticide Dust Diluents and Carriers", 2nd Ed., Darland Books, Caldwell N.J.; H. v. Olphen, "Introduction to Clay Colloid Chemistry", 2nd Ed., J. Wiley & Sons, N.Y.; Marsden, "Solvents Guide", 2nd Ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1967; Winnacker-Küchler, "Chemische Technologie" [Chemical Engineering], Volume 7, C. Hauser Verlag Munich, 4th Ed.1986.

Based on these formulations, it is also possible to prepare combinations with other pesticidally active substances, fertilizers and/or growth regulators, for example in the form of a ready mix or a tank mix. Wettable powders are preparations which are uniformly dispersible in water and which, beside the active substance, also comprise wetting agents, for example polyoxyethylated alkylphenols, polyoxyethylated fatty alcohols, alkyl- or alkylphenolsulfonates and dispersants, e.g. sodium lignosulfonate and sodium 2,2'-dinaphthylmethane6,6'-disulfonate, in addition to a diluent or inert substance. Emulsifiable concentrates are prepared by dissolving the active substance in an organic solvent, for example butanol, cyclohexanone, dimethylformamide, xylene, or else higher-boiling aromatics or hydrocarbons with addition of one or more emulsifiers. Emulsifiers which can be used are for example: calcium alkylarylsulfonates, such as calcium dodecylbenzenesulfonate, or nonionic emulsifiers such as, for example, fatty acid polyglycol esters, alkylaryl polyglycol ethers, fatty alcohol polyglycol ethers, propylene oxide/ethylene oxide condensates, alkyl polyethers, sorbitan fatty acid esters, polyoxyethylene sorbitan fatty acid esters or polyoxyethylene sorbitol esters.

Dusts are obtained by grinding the active substance with finely divided solid substances, for example talc, natural clays such as kaolin, bentonite, pyrophyllite or diatomaceous earth. Granules can be prepared either by spraying the active substance onto adsorptive granulated inert material or by applying active substance concentrates to the surface of carriers such as sand, kaolinites or granulated inert material with the aid of binders, for example polyvinyl alcohol, sodium polyacrylate or else mineral oils. Suitable active substances can also be granulated in the manner customary for the preparation of fertilizer granules, if desired in a mixture with fertilizers.

In wettable powders, the active substance concentration is, for example, approximately 10 to 90% by weight, the remainder to 100% being composed of customary formulation components. In the case of emulsifiable concentrates, the active substance concentration can amount to approximately 5 to 80% by weight. Formulations in the form of dusts usually comprise 5 to 20% by weight of active substance, sprayable solutions approximately 2 to 20% by weight. In the case of granules, the active substance content depends partly on whether the active compound is in liquid or solid form and on which granulation auxiliaries, fillers and the like are being used.

Additionally, the abovementioned formulations of active substances comprise, if appropriate, the tackifiers, wetting agents, dispersants, emulsifiers, penetrants, solvents, fillers or carriers which are customary in each case.

For use, the concentrates which are in commercially available form are, if appropriate, diluted in the customary manner, for example by means of water in the case of wettable powders, emulsifiable concentrates, dispersions and in some cases also microgranules. Preparations in the form of dusts and granules and sprayable solutions are usually not diluted further with other inert substances prior to use.

The rate of application required varies with the external conditions such as, inter alia, temperature and humidity. It can vary within wide limits, for example between 0.0005 and 10.0 kg/ha or more active substance, but it is preferably between 0.001 and 5 kg/ha.

The active substances according to the invention can be present in their commercially available formulations and in the use forms prepared from these formulations in the form of mixtures with other active substances, such as insecticides, attractants, sterilants, acaricides, nematicides, fungicides, ovicides, growth regulators or herbicides.

The pesticides include, for example, phosphoric esters, carbamates, carboxylic esters, formamidines, tin compounds, substances produced by microorganisms and the like.

Preferred components for mixtures are:
1. from the group of the phosphorus compounds acephate, azamethiphos, azinphosethyl, azinphosmethyl, bromophos, bromophosethyl, chlorfenvinphos, chlormephos, chlorpyrifos, chlorpyrifos-methyl, demeton, demeton-S-methyl, demeton-S-methylsulfone, dialifos, diazinon, dichlorvos, dicrotophos, O,O-1,2,2,2-tetrachloroethylphosphorothioate (SD 208 304), dimethoate, disulfoton, EPN, ethion, ethoprophos, etrimfos, famphur, fenamiphos, fenitriothion, fensulfothion, fenthion, fonofos, formothion, heptenophos, isozophos, isothioate, isoxathion, malathion, methacrifos, methamidophos, methidathion, salithion, mevinphos, monocrotophos, naled, omethoate, oxydemeton-methyl, parathion, parathion-methyl, phenthoate, phorate, phosalone, phosfolan, phosmet, phosphamidon, phoxim, pirimiphos, pirimiphos-ethyl, pirimiphos-methyl, profenofos, propaphos, proetamphos, prothiofos, pyraclofos, pyridapenthion, quinalphos, sulprofos, temephos, terbufos, tetrachlorvinphos, thiometon, triazophos, trichlorphon, vamidothion;
2. from the group of the carbamates aldicarb, 2-sec-butylphenyl methylcarbamate (BPMC), carbaryl, carbofuran, carbosulfan, cloethocarb, benfuracarb, ethiofencarb, furathiocarb, isoprocarb, methomyl, 5-methyl-m-cumenyl butyryl(methyl)carbamate, oxamyl, pirimicarb, propoxur, thiodicarb, thiofanox, ethyl 4,6,9-triaza4-benzyl-6,10-dimethyl-8-oxa-7-oxo-5,11-dithia-9-dodecenoate (OK 135), 1-methylthio(ethylideneamino)-N-methyl-N-(morpholinothio)carbamate (UC 51717);
3. from the group of the carboxylic esters allethrin, alphametrin, 5-benzyl-3-furylmethyl (E)-(1R)-cis, 2,2-dimethyl-3-(2-oxothiolan-3-ylidenemethyl)

cyclopropanecarboxylate, bioallethrin, bioallethrin ((S) cyclopentyl isomer), bioresmethrin, biphenate, (RS)-1-cyano-1-(6-phenoxy-2-pyridyl)methyl (1RS)-trans-3-(4-tert-butylphenyl)-2,2-dimethylcyclopropanecarboxylate (NCI 85193), cycloprothrin, cyhalothrin, cythithrin, cypermethrin, cyphenothrin, deltamethrin, empenthrin, esfenvalerate, fenfluthrin, fenpropathrin, fenvalerate, flucythrinate, flumethrin, fluvalinate (D isomer), permethrin, pheothrin ((R)-isomer), d-pralethrin, pyrethrins (natural products), resmethrin, tefluthrin, tetramethrin, tralomethrin;

4. from the group of the amidines amitraz, chlordimeform;
5. from the group of the tin compounds cyhexatin, fenbutatinoxide;
6. others abamectin, *Bacillus thuringiensis*, bensultap, binapacryl, bromopropylate, buprofezin, camphechlor, cartap, chlorobenzilate, chlorfluazuron, 2-(4-chlorophenyl)-4,5-diphenylthiophene (UBI-T 930), chlorfentezine, 2-naphthylmethyl cyclopropanecarboxylate (Ro12-0470), cyromazin, ethyl N-(3,5-dichloro4-(1,1,2,3,3,3-hexafluoro-1-propyloxy)phenyl)carbamoyl)-2-chlorobenzocarboximidate, DDT, Dicofol, N-(N-(3,5-dichloro4-(1,1,2,2-tetrafluoroethoxy)phenylamino) carbonyl)-2,6-difluorobenzamide (XRD 473), diflubenzuron, N-(2,3-dihydro-3-methyl-1,3-thiazol-2-ylidene)-2,4-xylidine, dinobuton, dinocap, endosulfan, ethofenprox, (4-ethoxyphenyl)(dimethyl)(3-(3-phenoxyphenyl)propyl)silane, (4-ethoxyphenyl)(3-(4-fluoro-3-phenoxyphenyl)propyl)dimethylsilane, fenoxycarb, 2-fluoro-5-(4-(4-ethoxyphenyl)-4-methyl-1-pentyl) diphenyl ether (MTI 800), granulosis and nuclear polyhedrosis viruses, fenthiocarb, flubenzimine, flucycloxuron, flufenoxuron, gamma-HCH, hexythiazox, hydramethylnon (AC 217300), ivermectin, 2-nitromethyl-4,5-dihydro-6H-thiazine (DS 52618), 2-nitromethyl-3,4-dihydrothiazole (SD 35651), 2-nitromethylene-1,2-thiazinan-3-ylcarbamaldehyde (WL 108477), propargite, teflubenzuron, tetradifon, tetrasul, thiocyclam, trifumuron, imidacloprid.

The active substance content of the use forms prepared from the commercially available formulations can range from 0.00000001 to 95% by weight of active substance, it is preferably between 0.00001 and 1% by weight.

They are applied in a customary manner adapted to the use forms.

The active substances according to the invention are also suitable for controlling endo- and ectoparasites in the field of veterinary medicine and in the field of animal keeping.

The active substances according to the invention are applied by oral administration, for example in the form of tablets, capsules, drinks, granules, by dermal administration, for example by dipping, spraying, pouring-on and spotting-on and dusting, and also by parenteral administration, for example by means of an injection, e.g. s.c.

Accordingly, the novel compound of the formula I according to the invention can also be employed especially advantageously in livestock keeping (for example cattle, sheep, pigs and poultry such as chickens, geese, and the like). In a preferred embodiment of the invention, the novel compounds are administered orally to the animals, if appropriate in the form of suitable formulations (cf. above) and if appropriate together with the drinking water or feed. Since elimination with the feces is efficient, this enables simple prevention of the development of insects in the animals' feces. The dosages and formulations which are suitable in each case depend, in particular, on the species and the developmental stage of the productive livestock and also on the degree of infection and can be readily determined and established by the customary methods. In the case of cattle, the novel compounds can be employed for example at dosages of from 0.01 to 1 mg/kg bodyweight.

The compounds of the formula I according to the invention are also distinguished by an outstanding fungicidal activity. Fungal pathogens which have already penetrated the plant tissue can be controlled successfully in a curative fashion. This is especially important and advantageous in the case of those fungal diseases which can no longer be controlled efficiently with the otherwise customary fungicides once infection has set in. The spectrum of action of the claimed compounds includes a variety of economically important phytopathogenic fungi such as, for example, *Plasmopara viticola, Phytophthora infestans, Erysiphe graminis, Pyricularia oryzae, Pyrenophora teres, Leptosphaeria nodorum* und *Pellicularia sasakii* and *Puccinia recondita*.

The compounds according to the invention are in addition also suitable for use in industrial fields, for example as wood preservatives, as preservatives in paints, in cooling lubricants for metalworking, or as preservatives in drilling and cutting oils.

The active substances according to the invention can be used in their commercially available formulations either alone or in combination with other fungicides known from the literature.

Fungicides known from the literature which can be combined in accordance with the invention with the compounds of the formula I are, for example, the following products:
aldimorph, andoprim, anilazine, BAS 480F, BAS 450F, BAS 490F, benalaxyl, benodanil, benomyl, binapacryl, bitertanol, bromuconazole, buthiobate, captafol, captan, carbendazim, carboxin, CGA 173506, cyprodinil, cyprofuram, dichlofluanid, dichlomezin, diclobutrazol, diethofencarb, difenconazole (CGA 169374), difluconazole, dimethirimol, dimethomorph, diniconazole, dinocap, dithianon, dodemorph, dodine, edifenfos, ethirimol, etridiazole, epoxiconazole, fenbuconazole, fenarimol, fenfuram, fenpiclonil, fenpropidin, fenpropimorph, fentin acetate, fentin hydroxide, ferimzone (TF164), fluazinam, fluobenzimine, fludioxinil, fluquinconazole, fluorimide, flusilazole, flutolanil, flutriafol, folpet, fosetyl-aluminum, fuberidazole, fulsulfamide (MT-F 651), furalaxyl, furconazole, furmecyclox, guazatine, hexaconazole, ICI A5504, imazalil, imibenconazole, iprobenfos, iprodione, isoprothiolane, KNF 317, copper compounds such as copper oxychloride, oxine-copper, copper oxide, mancozeb, maneb, mepanipyrim (KIF 3535), metconazol, mepronil, metalaxyl, methasulfocarb, methfuroxam, MON 24000, myclobutanil, nabam, nitrothalidopropyl, nuarimol, ofurace, oxadixyl, oxycarboxin, penconazole, pencycuron, PP 969, probenazole, propineb, prochloraz, procymidon, propamocarb, propiconazole, prothiocarb, pyracarbolid, pyrazophos, pyrifenox, pyrimethanil, pyroquilon, rabenzazole, RH7592, sulfur, tebuconazole, TF 167, thiabendazole, thicyofen, thiofanatemethyl, thiram, tolclofos-methyl, tolylfluanid, triadimefon, triadimenol, triazoxide, tricyclazole, tridemorph, triflumizole, triforine, trifionazol, validamycin, vinchlozolin, XRD 563, zineb, sodium dodecylsulfonate, sodium dodecyl sulfate, sodium C13/C15-alcohol ether sulfonate, sodium cetostearyl phosphate ester, sodium dioctylsulfosuccinate, sodium isopropylnaphthalenesulfonate, sodium methylenebisnaphthalenesulfonate, cetyltrimethylammonium chloride, salts of long-chain primary, secondary or tertiary amines, alkylpropyleneamines, laurylpyrimidinium bromide, ethoxylated quaternized fatty amines, alkyldimethylbenzylammonium chloride and 1-hydroxyethyl-2-alkyl-imidazoline.

The abovementioned components in combinations are known active substances, many of which are described in Ch.R Worthing, S. B. Walker, The Pesticide Manual, 7th edition (1983), British Crop Protection Council. The active substance content of the use forms prepared from the commercially available formulations can vary within wide ranges, the active substance concentration of the use forms can amount to from 0.0001 to 95% by weight of active substance, it is preferably between 0.0001 and 1% by weight. They are applied in a customary manner adapted to suit the use forms.

The examples which follow are intended to illustrate the invention without imposing any limitation thereto.

A. Formulation Examples a) A dust was obtained by mixing 10 parts by weight of active substance and 90 parts by weight of talc as inert substance and comminuting the mixture in a hammer mill.

b) A wettable powder which was readily dispersible in water was obtained by mixing 25 parts by weight of active substance, 65 parts by weight of kaolin-containing quartz as inert substance, 10 parts by weight of potassium lignosulfonate and 1 part by weight of sodium oleoylmethyltaurinate as wetting agent and dispersant and grinding the mixture in a pinned-disk mill.

c) A dispersion concentrate which is readily dispersible in water was prepared by mixing 40 parts by weight of active substance with 7 parts by weight of a sulfosuccinic monoester, 2 parts by weight of a sodium lignosulfosuccinate and 51 parts by weight of water and grinding the mixture in a ball mill to a fineness of below 5 microns.

d) An emulsifiable concentrate was prepared from 15 parts by weight of active substance, 75 parts by weight of cyclohexane as solvent and 10 parts by weight of oxyethylated nonylphenol (10 EO) as emulsifier.

e) Granules were prepared from 2 to 15 parts by weight of active substance and an inert carrier material for granules such as attapulgite, pumice granules and/or quartz sand. Expediently, a suspension of the wettable powder from Example b) with a solids content of 30% was used; this was sprayed onto the surface of attapulgite granules and the latter were dried and mixed intimately. The wettable powder amounted to approximately 5% by weight and the inert carrier material to approximately 95% of the finished granules.

B. Preparation Examples

EXAMPLE A

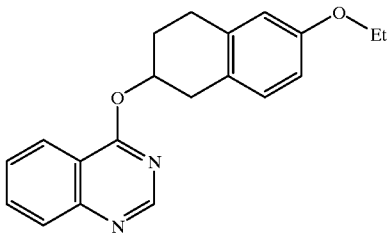

4-(6-Ethoxytetralin-2-yloxy)quinazoline 2.57 g (13.3 mmol) of 6-ethoxytetralin-2-ol in 5 ml of THF were added, with ice-cooling, to a suspension of 400 mg of NaH (80% pure, 13.3 mmol in 40 ml of THF). The mixture was subsequently refluxed for 1 hour and cooled to room temperature, and 2.0 g (12.2 mmol) of 4-chloroquinazoline were added. The mixture was refluxed for 24 hours and cooled and then diluted with ether and washed with saturated sodium hydrogen carbonate and saturated sodium chloride solution. After the organic phase had been dried and concentrated, the residue was chromatographed on silica gel using petroleum ether/ethyl acetate (9:1, 8:2). This gave 2.39 g (61% of theory) of colorless crystals (m.p.115–117° C.).

Preparation of 6-ethoxytetralin-2-ol 1.97 g (52 mmol) of sodium borohydride were added in portions of 0° C. to 9.8 g (51.4 mmol) of 6-ethoxy-2-tetralone in 150 ml of ethanol. The mixture was stirred for 1 hour at 0° C. and diluted with 200 ml of 2N sodium hydroxide solution, and the solution was extracted with dichloromethane. The combined organic phases were washed with saturated sodium chloride solution, dried and concentrated. This gave 9.8 g of an oil which was further reacted without purification.

Preparation of 6-ethoxy-2-tetralone 39.1 g (0.20 mol) of 4-ethoxyphenylacetyl chloride in 200 ml of dichloromethane were added dropwise in the course of 1 hour at −78° C. to 53.4 g (0.4 mol) of aluminum chloride in 800 ml of dichloromethane. A vigorous stream of ethylene was subsequently passed in in the course of 15 minutes, and the mixture was allowed to come to room temperature and stirred for a further 3 hours. The dark red solution was cooled to 0° C. and carefully treated with 300 ml of ice-water. After phase separation, the organic phase was washed with 2N HCl (3×) and saturated sodium hydrogen carbonate solution, dried and evaporated on a rotary evaporator. After purification by column chromatography with petroleum ether/ethyl acetate (9:1, 8:2), 20.9 g (56% of theory) of a yellow syrup were obtained.

Preparation of 4-ethoxyphenylacetyl chloride 50 g (0.28 mol) of 4-ethoxyphenylacetic acid were treated with 50 ml of thionyl chloride and the mixture was stirred for 24 hours at room temperature. Excess thionyl chloride was removed in vacuo and the residue was distilled under a high vacuum. This gave 39 g (71% of theory) of an oil (boiling point 110° C./53.3 Pa).

EXAMPLE B

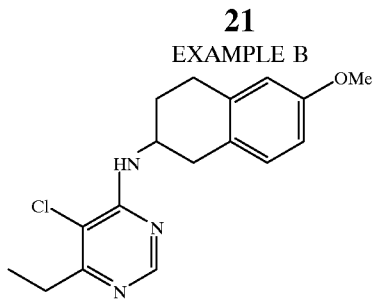

5-Chloro-6-ethyl-4-(6-methoxytetralin-2-ylamino) pyrimidine 1.5 g (8.5 mmol) of 4,5-dichloro-6-ethylpyrimidine, 1.5 g (8.5 mmol) of 2-amino-6-methoxytetralin and 2 ml of triethylamine were heated for 10 hours at 85° C. The mixture was subsequently diluted with water and ether, the phases were separated, and the organic phase was washed with water and saturated NaCl solution. After the mixture had been dried and concentrated, the residue was purified by column chromatography with petroleum ether/ethyl acetate (8:1). This gave 2.4 g (89% of theory) of colorless crystals (melting point 70–71° C.).

Preparation of 2-amino-6-methoxytetralin 6.0 g (30 mmol) of 2-azido-6-methoxytetralin 15 ml of TMF were added dropwise in the course of 15 minutes at 0° C. to a suspension of 1.7 g (44 mmol) of lithium aluminum hydride in 70 ml of THF. The mixture was stirred for 30 minutes at room temperature and refluxed for 1 hour. After cooling to 0° C., excess alanate was destroyed with isopropanol, and the mixture was diluted with ether and washed with saturated tartrate and saturated NaCl solution. After the organic phase had been dried and concentrated, the resulting colorless oil was further employed directly. Yield 5.1 g (96% of theory).

Preparation of 2-azido-6-methoxytetralin 8.0 g (31 mmol) of 2-methanesulfonyloxy-6-methoxytetralin and 2.6 g (40 mmol) of sodium azide were heated for 3 hours at 90° C. in 100 ml of DMF. After the mixture had been cooled, it was diluted with ether, washed with water and saturated NaCl solution, dried and concentrated in vacuo. This gave 6 g (95% of theory) of a colorless oil which was further reacted directly.

Preparation of 2-methanesulfonyloxy-6-methoxytetralin 4.5 g (39 mmol) of methanesulfonyl chloride were added dropwise at 0° C. to a solution of 5.4 g (30 mmol) of 6-methoxytetralin-2-ol and 4.6 g (45 mmol) of triethylamine in 60 ml of dichloromethane. The mixture was stirred for 1 hour at 0° C. and then washed with water, 2N HCl, saturated NaHCO$_3$ solution and saturated NaCl solution. After the mixture had been dried and concentrated, 8 g (97% of theory) of mesylate were obtained, and this was further reacted without purification.

EXAMPLE C

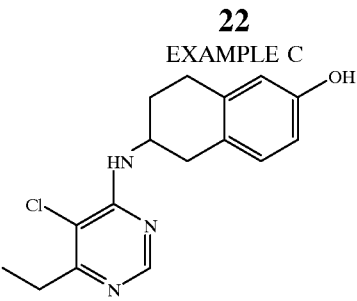

5-Chloro-6-ethyl-4-(6-hydroxytetralin-2-ylamino) pyrimidine

A solution of 5.8 g (18 mmol) of 5-chloro6-ethyl4-(6-methoxytetralin-2-ylamino)pyrimidine in 22 ml of 48% HBr and 4.5 ml of acetic acid was heated for 4 hours at 110° C. After the mixture had cooled, it was brought to pH=8 with sodium hydroxide solution and extracted with dichloromethane. After the dichloromethane phase had been dried, concentrated and washed with toluene, 4.8 g (88% of theory) of colorless crystals were obtained (m.p. 178° C.).

EXAMPLE D

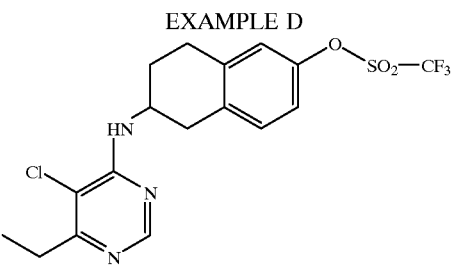

5-Chloro-6-ethyl-4-(6-trifluoromethylsulfonyloxytetralin-2-ylamino) pyrimidine 1.55 g (5.5 mmol) of trifluoromethanesulfonyl anhydride were added at 0° C. to a solution of 1.2 g (4.0 mmol) of 5-chloro-6-ethyl-4-(6-hydroxytetralin-2-ylamino) pyrimidine in 5 ml of pyridine. The mixture was stirred for 2 hours at room temperature, diluted with dichloromethane and washed with saturated NaHCO$_3$ solution. After the dichloromethane phase had been dried, concentrated and purified by column chromatography with petroleum ether/ethyl acetate (7:3), 1.0 g (57% of theory) of a colorless oil were obtained.

The compounds of the tables which follow were obtained analagously to Examples A to D:

TABLE 1

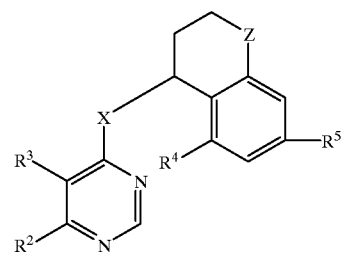

| Ex. No. | R$^2$ | R$^3$ | X | Z | R$^4$ | R$^5$ | m.p. [° C.] |
|---|---|---|---|---|---|---|---|
| 1 | C$_2$H$_5$ | Cl | NH | CH$_2$ | H | H | |
| 2 | CH$_3$OCH$_2$ | OCH$_3$ | NH | CH$_2$ | H | H | 135–137 |

TABLE 1-continued

| Ex. No. | $R^2$ | $R^3$ | X | Z | $R^4$ | $R^5$ | m.p. [°C.] |
|---|---|---|---|---|---|---|---|
| 3 | $C_2H_5$ | Cl | O | $CH_2$ | H | H | |
| 4 | $CH_3OCH_2$ | $OCH_3$ | O | $CH_2$ | H | H | |
| 5 | $C_2H_5$ | Cl | NH | O | H | H | |
| 6 | $CH_3OCH_2$ | $OCH_3$ | NH | O | H | H | 152–153 |
| 7 | $CH_3OCH_2$ | $OCH_3$ | NH | S | H | H | 142–144 |
| 8 | $C_2H_5$ | Cl | O | S | H | H | |
| 9 | $C_2H_5$ | Cl | NH | S | $CH_3$ | $CH_3$ | 135 |
| 10 | $C_2H_5$ | Cl | O | S | $CH_3$ | $CH_3$ | |

TABLE 2

| Ex. No. | $R^2$ | $R^3$ | X | $R^4$ | $R^5$ | m.p. [°C.] |
|---|---|---|---|---|---|---|
| 11 | $C_2H_5$ | Cl | O | H | H | 85 |
| 12 | $C_2H_5$ | Cl | NH | H | H | |
| 13 | $CH_3OCH_2$ | $OCH_3$ | O | H | H | 48 |
| 14 | $CH_3OCH_2$ | $OCH_3$ | NH | H | H | 101–103 |
| 15 | $(CH)_4$ | | O | H | H | 59 |
| 16 | $(CH)_4$ | | NH | H | H | |
| 17 | $(CH_2)_4$ | | O | H | H | 110 |
| 18 | $(CH_2)_4$ | | NH | H | H | |
| 19 | $C_2H_5$ | Cl | NH | $OCH_3$ | H | |
| 20 | $(CH)_4$ | | NH | $OCH_3$ | H | |
| 21 | $(CH)_4$ | | O | $OCH_3$ | H | |

TABLE 2-continued

| Ex. No. | $R^2$ | $R^3$ | X | $R^4$ | $R^5$ | m.p. [°C.] |
|---|---|---|---|---|---|---|
| 22 | $C_2H_5$ | Cl | NH | $OC_2H_5$ | H | |
| 23 | $C_2H_5$ | Cl | NH | $OCH_2O$ | | |

TABLE 3

| Ex. No. | $R^2$ | $R^3$ | X | $R^4$ | $R^5$ | m.p. [°C.] |
|---|---|---|---|---|---|---|
| 24 | $C_2H_5$ | Cl | O | H | H | oil |
| 25 | $C_2H_5$ | Cl | NH | H | H | |
| 26 | $CH_3OCH_2$ | $OCH_3$ | O | H | H | oil |
| 27 | $CH_3OCH_2$ | $OCH_3$ | NH | H | H | |
| 28 | $(CH)_4$ | | O | H | H | 119–121 |
| 29 | $(CH)_4$ | | NH | H | H | |
| 30 | $(CH_2)_4$ | | O | H | H | oil |
| 31 | $(CH_2)_4$ | | NH | H | H | |
| 32 | $C_2H_5$ | Cl | O | $OCH_3$ | H | |
| 33 | $C_2H_5$ | Cl | NH | $OCH_3$ | H | |
| 34 | $(CH)_4$ | | O | $OCH_3$ | H | |
| 35 | $C_2H_5$ | Cl | NH | $OC_2H_5$ | H | |
| 36 | $C_2H_5$ | Cl | NH | $OCH_2O$ | | |

TABLE 4

| Ex. No. | $R^2$ | $R^3$ | X | $R^4$ | $R^5$ | $R^6$ | m.p. [°C.] |
|---|---|---|---|---|---|---|---|
| 37 | $C_2H_5$ | Cl | O | H | H | H | oil |
| 38 | $C_2H_5$ | Cl | NH | H | H | H | 80–82 |

TABLE 4-continued

| Ex. No. | R² | R³ | X | R⁴ | R⁵ | R⁶ | m.p. [° C.] |
|---|---|---|---|---|---|---|---|
| 39 | CH₃OCH₂ | OCH₃ | O | H | H | H | oil |
| 40 | CH₃OCH₂ | OCH₃ | NH | H | H | H | 115–116 |
| 41 | (CH)₄ | | O | H | H | H | 75 |
| 42 | (CH)₄ | | NH | H | H | H | |
| 43 | CF—(CH)₃ | | O | H | H | H | |
| 44 | CCl—(CH)₃ | | O | H | H | H | |
| 45 | (CH₂)₄ | | O | H | H | H | oil |
| 46 | (CH₂)₄ | | NH | H | H | H | |
| 47 | C₂H₅ | Cl | O | H | H | OCH₃ | 45–48 |
| 48 | C₂H₅ | Cl | NH | H | H | OCH₃ | 70–71 |
| 49 | CH₃OCH₂ | OCH₃ | O | H | H | OCH₃ | oil |
| 50 | CH₃OCH₂ | OCH₃ | NH | H | H | OCH₃ | oil |
| 51 | (CH)₄ | | O | H | H | OCH₃ | 114–115 |
| 52 | (CH)₄ | | NH | H | H | OCH₃ | 165–166 |
| 53 | CF—(CH)₃ | | NH | H | H | OCH₃ | 200 |
| 54 | CF—(CH)₃ | | O | H | H | OCH₃ | |
| 55 | (CH₂)₄ | | O | H | H | OCH₃ | 87–88 |
| 56 | C₂H₅ | Cl | O | H | H | OC₂H₅ | 64–67 |
| 57 | C₂H₅ | Cl | NH | H | H | OC₂H₅ | 100 |
| 58 | CH₃OCH₂ | OCH₃ | O | H | H | OC₂H₅ | oil |
| 59 | CH₃OCH₂ | OCH₃ | NH | H | H | OC₂H₅ | oil |
| 60 | (CH)₄ | | O | H | H | OC₂H₅ | 115–117 |
| 61 | (CH)₄ | | NH | H | H | OC₂H₅ | |
| 62 | CF(CH)₃ | | O | H | H | OC₂H₅ | 104 |
| 63 | CCl(CH)₃ | | O | H | H | OC₂H₅ | 126–128 |
| 64 | (CH₂)₄ | | O | H | H | OC₂H₅ | |
| 65 | C₂H₅ | Cl | O | H | H | OH | |
| 66 | C₂H₅ | Cl | NH | H | H | OH | 178 |
| 67 | (CH)₄ | | O | H | H | OH | |
| 68 | C₂H₅ | | O | H | H | O-n-C₃H₇ | |
| 69 | C₂H₅ | | NH | H | H | O-n-C₃H₇ | |
| 70 | (CH)₄ | | O | H | H | O-n-C₃H₇ | |
| 71 | (CH)₄ | | NH | H | H | O-n-C₃H₇ | |
| 72 | C₂H₅ | Cl | O | H | H | O-i-C₃H₇ | |
| 73 | C₂H₅ | Cl | NH | H | H | O-i-C₃H₇ | oil |
| 74 | (CH)₄ | | O | H | H | O-i-C₃H₇ | oil |
| 75 | (CH)₄ | | NH | H | H | O-i-C₃H₇ | 147 |
| 76 | CF(CH)₃ | | O | H | H | O-i-C₃H₇ | oil |
| 77 | CF(CH)₃ | | NH | H | H | O-i-C₃H₇ | 187 |
| 78 | CCl(CH)₃ | | NH | H | H | O-i-C₃H₇ | 133 |
| 79 | C₂H₅ | H | O | H | H | O-i-C₃H₇ | oil |
| 80 | C₂H₅ | Cl | O | H | H | O—CH₂(C₂H₃) | |
| 81 | C₂H₅ | Cl | NH | H | H | O—CH₂(C₂H₃) | |
| 82 | (CH)₄ | | O | H | H | O—CH₂(C₂H₃) | 94 |
| 83 | CF(CH)₃ | | O | H | H | O—CH₂(C₂H₃) | |
| 84 | C₂H₅ | Cl | O | H | H | O—CH₂(C₂H₃) | |
| 85 | C₂H₅ | Cl | NH | H | H | O—CH₂(C₂H₃) | |
| 86 | (CH)₄ | | O | H | H | O—CH₂(C₂H₃) | 72 |
| 87 | CF(CH)₃ | | O | H | H | O—CH₂(C₂H₃) | |
| 88 | C₂H₅ | Cl | NH | H | H | O-s-C₄H₉ | oil |
| 89 | C₂H₅ | Cl | O | H | H | O-s-C₄H₉ | |
| 90 | (CH)₄ | | NH | H | H | O-s-C₄H₉ | 185 |
| 91 | (CH)₄ | | O | H | H | O-s-C₄H₉ | |
| 92 | CF(CH)₃ | | NH | H | H | O-s-C₄H₉ | 108 |
| 93 | CF(CH)₃ | | O | H | H | O-s-C₄H₉ | |
| 94 | C₂H₅ | H | O | H | H | O-s-C₄H₉ | oil |
| 95 | C₂H₅ | Cl | NH | H | H | O-t-C₄H₉ | oil |
| 96 | C₂H₅ | Cl | NH | H | H | OC₂H₄OCH₃ | |
| 97 | C₂H₅ | Cl | O | H | H | OC₂H₄OCH₃ | oil |
| 98 | (CH)₄ | | NH | H | H | OC₂H₄OCH₃ | |
| 99 | (CH)₄ | | O | H | H | OC₂H₄OCH₃ | oil |
| 100 | C₂H₅ | Cl | O | H | H | O-benzyl | 67 |
| 101 | C₂H₅ | Cl | NH | H | H | O-benzyl | |
| 102 | (CH)₄ | | O | H | H | O-benzyl | 89 |

TABLE 4-continued

| Ex. No. | R² | R³ | X | R⁴ | R⁵ | R⁶ | m.p. [° C.] |
|---|---|---|---|---|---|---|---|
| 103 | CF(CH)₃ | | O | H | H | O-benzyl | 118 |
| 104 | CCl(CH)₃ | | O | H | H | O-benzyl | 119 |
| 105 | C₂H₅ | Cl | O | H | H | 4-NO₂-phenoxy | 98 |
| 106 | (CH)₄ | | O | H | H | 4-NO₂-phenoxy | 149 |
| 107 | CF(CH)₃ | | O | H | H | 4-NO₂-phenoxy | 153 |
| 108 | (CH)₄ | | O | H | H | 2-NO₂-phenoxy | oil |
| 109 | C₂H₅ | Cl | O | H | H | 4-Cl-phenoxy | oil |
| 110 | (CH)₄ | | O | H | H | 4-Cl-phenoxy | oil |
| 111 | C₂H₅ | Cl | NH | H | H | 4-CF₃-phenoxy | oil |
| 112 | C₂H₅ | Cl | NH | H | H | pyridin-2-yloxy | oil |
| 113 | C₂H₅ | Cl | NH | H | H | 5-CF₃-pyridin-2-yloxy | 95 |
| 114 | C₂H₅ | Cl | NH | H | H | 3-CN-pyridin-2-yloxy | 188 |
| 115 | C₂H₅ | Cl | NH | H | H | pyrimidin-2-yloxy | 100 |
| 116 | (CH)₄ | | O | H | H | CMF₂ | oil |
| 117 | C₂H₅ | | O | H | H | OCF₂CF₂Br | oil |
| 118 | (CH)₄ | | O | H | H | OCF₂CF₂Br | oil |
| 119 | CF(CH)₃ | | O | H | H | OCF₂CF₂Br | 87 |
| 120 | C₂H₅ | Cl | NH | H | H | OCH₂CO₂-t-C₄H₉ | oil |
| 121 | C₂H₅ | Cl | NH | H | H | OCO₂C₂H₅ | 96 |
| 122 | C₂H₅ | Cl | NH | H | H | OCONHCH₃ | 210 |
| 123 | C₂H₅ | Cl | O | H | H | OCON(CH₃)₂ | |
| 124 | C₂H₅ | Cl | NH | H | H | OCON(CH₃)₂ | 129 |
| 125 | C₂H₅ | Cl | NH | H | H | OCONMEt | 180 |
| 126 | C₂H₅ | Cl | NH | H | H | OCONEt₂ | 93 |
| 127 | C₂H₅ | Cl | NH | H | H | OCO—N-pyrrolidinyl | 150 |
| 128 | C₂H₅ | Cl | NH | H | H | OCO—N-morpholinyl | 159 |
| 129 | C₂H₅ | Cl | NH | H | H | OCONHcyclo-hexyl | 186 |
| 130 | C₂H₅ | Cl | NH | H | H | OCONH-t-butyl | 126 |
| 131 | C₂H₅ | Cl | NH | H | H | OCON-(i-propyl)₂ | |
| 132 | C₂H₅ | Cl | O | H | H | OCONHC₆H₅ | |
| 133 | C₂H₅ | Cl | NH | H | H | OCONHC₆H₅ | 140 |
| 134 | (CH)₄ | | O | H | H | OCON(CH₃)C₆H₅ | |
| 135 | C₂H₅ | Cl | NH | H | H | OCON(CH)₃C₆H₅ | 146 |
| 136 | C₂H₅ | Cl | O | H | H | OSO₂CH₃ | oil |
| 137 | C₂H₅ | Cl | NH | H | H | OSO₂CH₃ | oil |
| 138 | (CH)₄ | | O | H | H | OCO₂CH₃ | |
| 139 | CF(CH)₃ | | O | H | H | OCO₂CH₃ | 173 |
| 140 | C₂H₅ | Cl | O | H | H | OSO₂C₃H₇ | |
| 141 | C₂H₅ | Cl | NH | H | H | OSO₂C₃H₇ | oil |
| 142 | C₂H₅ | Cl | O | H | H | OSO₂CF₃ | |
| 143 | C₂H₅ | Cl | NH | H | H | OSO₂CF₃ | oil |
| 144 | (CH)₄ | | O | H | H | OSO₂N(CH₃)₂ | oil |
| 145 | C₂H₅ | Cl | O | H | H | F | 96 |
| 146 | (CH)₄ | | O | H | H | F | 93 |
| 147 | C₂H₅ | Cl | NH | H | H | Cl | 125–126 |
| 148 | CH₃OCH₂ | OCH₃ | NH | H | H | Cl | 131–132 |
| 149 | CH₃OCH₂ | OCH₃ | O | H | H | Cl | |
| 150 | C₂H₅ | Cl | O | H | H | Br | |
| 151 | (CH)₄ | | O | H | H | Br | 125 |
| 152 | C₂H₅ | Cl | O | H | H | CN | 107 |
| 153 | (CH)₄ | | O | H | H | CN | 125 |
| 154 | CF(CH)₃ | | O | H | H | CN | 160 |
| 155 | CCl(CH)₃ | | O | H | H | CN | 200 |
| 156 | C₂H₅ | Cl | O | H | H | CONH₂ | 148 |
| 157 | (CH)₄ | | O | H | H | CONH₂ | 175 |
| 158 | CF(CH)₃ | | O | H | H | CONH₂ | 210 |
| 159 | (CH)₄ | | O | H | H | CONHC₆H₅ | oil |
| 160 | (CH)₄ | | O | H | H | COOCH₃ | oil |
| 161 | C₂H₅ | Cl | O | H | H | COCH₃ | oil |
| 162 | (CH)₄ | | O | H | H | COCH₃ | 104 |
| 163 | C₂H₅ | Cl | NH | H | H | OPO(OEt)₂ | oil |
| 164 | C₂H₅ | Cl | NH | H | H | OPS(OCH₃)₂ | oil |
| 165 | C₂H₅ | Cl | NH | H | H | CH₃ | |
| 166 | C₂H₅ | Cl | NH | H | H | i-C₃H₇ | oil |

TABLE 4-continued

| Ex. No. | $R^2$ | $R^3$ | X | $R^4$ | $R^5$ | $R^6$ | m.p. [° C.] |
|---|---|---|---|---|---|---|---|
| 167 | $C_2H_5$ | Cl | O | H | H | $i\text{-}C_3H_7$ | oil |
| 168 | $(CH)_4$ | | NH | H | H | $i\text{-}C_3H_7$ | 166 |
| 169 | $(CH)_4$ | | O | H | H | $i\text{-}C_3H_7$ | |
| 170 | $CF(CH)_3$ | | O | H | H | $i\text{-}C_3H_7$ | oil |
| 171 | $C_2H_5$ | H | O | H | H | $i\text{-}C_3H_7$ | oil |
| 172 | $C_2H_5$ | Cl | NH | H | $OCH_3$ | H | |
| 173 | $(CH)_4$ | | NH | H | $O\text{-}i\text{-}C_3H_7$ | H | oil |

TABLE 5

| Ex. No. | $R^2$ | $R^3$ | $R^4$ | $R^5$ | $R^6$ | $R^7$ | m.p. [° C.] |
|---|---|---|---|---|---|---|---|
| 174 | $C_2H_5$ | Cl | H | H | H | H | oil |
| 175 | $CH_3OCH_2$ | $OCH_3$ | H | H | H | H | 111 |
| 176 | $(CH)_4$ | | H | H | H | H | 231 |
| 177 | $C_2H_5$ | Cl | H | $CH_3$ | H | H | 73 |
| 178 | $CH_3OCH_2$ | $OCH_3$ | H | $CH_3$ | H | H | 106 |
| 179 | $C_2H_5$ | Cl | $OCH_3$ | H | $OCH_3$ | H | 64 |
| 180 | $C_2H_5$ | Cl | $OCH_3$ | H | H | H | |
| 181 | $C_2H_5$ | Cl | H | H | H | $OCH_3$ | |
| 182 | $C_2H_5$ | Cl | H | $C_2H_5$ | H | H | |
| 183 | $C_2H_5$ | Cl | H | H | $OSO_2CH_3$ | H | |
| 184 | $C_2H_5$ | Cl | H | H | $OSO_2CF_3$ | H | |
| 185 | $C_2H_5$ | Cl | H | H | $OSO_2CF_3$ | H | |
| 186 | $C_2H_5$ | Cl | H | H | $OCON(CH_3)_2$ | H | |
| 187 | $C_2H_5$ | Cl | H | H | $OSO_2C_3H_7$ | H | |

C. Biological Examples

Use as fungicide

The activity of the preparations according to the invention was assessed using a 0–4 scale, in which 0 means a disease suppression of 0–24%
1 means a disease suppression of 25–49%
2 means a disease suppression of 50–74%
3 means a disease suppression of 75–97%
4 means a disease suppression of 97–100%.

EXAMPLE F

Barley plants cv. "Maris Otter" in the 2-leaf stage were sprayed to run-off with a solution of the compound according to the invention in a mixture of 40% of acetone and 60% of water. 24 hours later, the plants were inoculated with conidia of powdery mildew of barley (*Erysiphe graminis* f. sp. *hordei*) and kept in a controlled-environment cabinet at 20° C. and a relative atmospheric humidity of 75–80%. 7 days after the treatment, the plants were examined for symptoms of powdery mildew of barley. The following compounds scored 3 or 4 at 500 mg of active substance/l spray mixture:

Compounds of Examples No. 58, 60, 61 and 148.

EXAMPLE G

Tomato plants cv."First in the Field" in the 3–4-leaf stage were sprayed to run-off with a solution of the compound according to the invention in a mixture of 40% of acetone and 60% of water. 24 hours later, the plants were inoculated with a spore suspension of *Phytophthora infestans* (20,000 spores/ml) and kept in a controlled-environment cabinet at 15° C., first for 2 days at a relative atmospheric humidity of 99% and then for 4 days at a relative atmospheric humidity of 75–80%. 6 days after the treatment, the plants were examined for symptoms of Phytophthora infestans. The following compounds scored 3 or 4 at 500 mg of active substance/l spray mixture:

Compounds of Examples No. 49, 52, 56 and 148.

EXAMPLE H

Grapevine seedlings cv."Grüner Veltliner" approximately 6 weeks old were sprayed to run-off with a solution of the compound according to the invention in a mixture of 40% of acetone and 60% of water. 24 hours later, the plants were inoculated by spraying with a zoospore suspension (100,000/ ml) of *Plasmopara viticola and* kept in a controlled-environment cabinet at 70° C. and a relative atmospheric humidity of approximately 99%. 14 days after the treatment, the plants were examined for symptoms of *Plasmopara viticola*. The following compounds scored 3 or 4 at 500 mg of active substance/l spray mixture:

Compounds of Examples No. 48, 49, 52, 53, 56, 57, 59, 60, 61, 62, 64, 73, 75, 76, 77, 82, 86, 88, 90, 92, 97, 99, 100, 102, 103, 104, 106, 108, 112, 113, 114, 118, 121, 124, 126, 128, 131, 133, 136, 137, 139, 140, 141, 154, 155, 158, 159, 160, 161, 166, 168, 170, 171, 177 and 179.

EXAMPLE I

Wheat plants cv. "Hornet" in the 2-leaf stage were sprayed to run-off with a solution of the compound according to the invention in a mixture of 40% of acetone and 60% of water. 24 hours later, the plants were inoculated by spraying with a pyknospore suspension (500,000/ml) of *Leptosphaeria nodorum* and kept in a controlled-environment cabinet at 18–20° C. and a relative atmospheric humidity of approximately 99%. 14 days after inoculation, the plants were examined for symptoms of *Leptosphaeria nodorum*. The following compounds scored 3 or 4 at 500 mg of active substance/l spray mixture:

Compounds of Examples No. 52, 53, 60, 62, 73, 75, 77, 78, 79, 86, 88, 90, 92, 94, 99, 100, 102, 103, 106, 107, 108, 110, 111, 113, 115, 119, 122, 125, 126, 130, 131, 133, 135, 139, 141, 143, 144, 148, 157, 158, 159, 166, 167, 168 and 176.

EXAMPLE K

Rice plants cv. "Nihonbare" in the 1.5-leaf stage were sprayed to run-off with a solution of the compound according to the invention in a mixture of 40% of acetone and 60% of water. A solution of the substance in a mixture of 5% of acetone and 95% of water was applied simultaneously by pouring. 24 hours later, the plants were inoculated by spraying with a pyknospore suspension ($10^6$/ml) of *Pyricularia oryzae*. The plants were kept for 2 days in a darkened controlled-environment cabinet at 26° C. and a relative atmospheric humidity of 99% and subsequently transferred into an illuminated controlled-environment cabinet at approximately 18° C. and a relative atmospheric humidity of 75–80%. 7–9 days after inoculation, the plants were examined for symptoms of *Pyricularia oryzae*. The following substances scored 3 or 4 at 500 mg of active substance/l spray mixture:

Compounds of Examples No. 48, 49, 57, 58, 60, 61, 66, 73, 74, 76, 78, 82, 94, 97, 99, 100, 102, 103, 104, 109, 110, 112, 113, 114, 116, 118, 119, 126, 128, 136, 139, 141, 143, 144, 151, 160, 167, 168, 170, 171, 174, 175, 176, 177 and 179.

EXAMPLE L

Apple seedlings (Malus sp.) approximately 3 weeks old were sprayed to run-off with a solution of the compound according to the invention in a mixture of 40% of acetone and 60% of water. After 24 hours, the plants were inoculated by spraying with a spore suspension (300,000/ml) of *Venturia inaequalis*. The plants were kept for 2 days in the dark at 18–20° C. and a relative atmospheric humidity of 99%, subsequently in the light for 5 days at the same atmospheric humidity and finally for 7 days at an atmospheric humidity of 75–80%. 14 days after the treatment, the plants were examined for symptoms of *Venturia inaequalis*. The following substances scored 3 or 4 at 500 mg of active substance/l of spray mixture:

Compounds according to Examples No. 73, 174 and 175.

EXAMPLE M

Tomato plants cv. "First in the Field" in the 2–3-leaf stage were sprayed to run-off with a solution of the compound according to the invention in a mixture of 40% of acetone and 60% of water. After 24 hours, the plants were inoculated with a spore suspension (500,000/ml) of *Botrytis cinerea*. The plants were kept in a controlled-environment cabinet at 18–20° C. and a relative atmospheric humidity of 99%. 5 days after inoculation, the plants were examined for symptoms of *Botrytis cinerea*. The following substances scored 3 or 4 at 500 mg of active substance/l spray mixture:

Compounds of Examples No. 73 and 175.

EXAMPLE N

Wheat cv. "Jubilar" in the 2-leaf stage was treated to run-off with aqueous suspensions of the claimed compounds. After the spray coating had dried on, the plants were inoculated with an aqueous spore suspension of *Puccinia recondita*. The plants, treated to run-off, were placed for approximately 16 hours into a controlled-environment cabinet at 20° C. and an atmospheric humidity of approximately 100%. They were then grown on in a greenhouse at a temperature of 22 to 25° C. and a relative atmospheric humidity of 50 to 70%. After an incubation time of approximately 2 weeks, the fungus sporulated on the entire leaf surface of the untreated control plants (infection level 100%) so that it was possible to assess the disease level of the test plants. The disease level was expressed in % diseased leaf area in comparison with the untreated control plants, which showed an infection level of 100%. The following compounds scored 3 or 4 at 500 mg of active substance/l spray mixture:

Compounds of Examples No. 13, 14, 38, 39, 40, 48 and 50.

Use as insecticide/acaricide

EXAMPLE O

Portions of 1 ml of the test formulation, emulsified in water, were applied uniformly to the insides of the dish and of the cover of a Petri dish and, after the coating had dried on, batches of 10 imagines of the common housefly (*Musca domestica*) were introduced. After the dishes had been closed, they were kept at room temperatures, and the mortality of the test animals was determined after 3 hours. At 300 ppm (active substance content in the test solution), the preparations of Examples No. 50, 57, 59, 73, 124, 137 and 179 showed 100% mortality of the test animals which had been introduced.

EXAMPLE P

Rice seeds were germinated on cotton wool in glass culture dishes under moist conditions and, after they had grown to a stem length of approximately 8 cm, were introduced with the leaves into the test solution. After the solution had run off, the treated rice plants were introduced into culture containers separately for each test concentration and populated with batches of 10 larvae (L3) of the species *Nilaparvata lugens*. After the sealed culture containers had been kept at 21° C., the mortality of the leafhopper larvae was determined after 4 days. At a concentration of 300 ppm (active substance content in the test solution), 100% mortality of the test animals introduced was shown by the preparations of Examples No. 59, 61, 73, 137, 141, 179, 111, 95, 166, 126, 97 and 99.

EXAMPLE Q

Wheat seed was pregerminated for 6 hours under water and then transferred into 10 ml glass test tubes and covered with 2 ml of soil in each case. After 1 ml of water had been added, the plants remained in the culture tubes at room temperature (21° C.) until they had reached a plant height of approximately 3 cm. *Diabrotica undecimpunctata* larvae in the middle stage (batches of 10) were subsequently introduced onto the soil in the glass tubes and, after 2 hours, 1 ml of the test liquid in the concentration to be tested was pipetted onto the soil surface in the glass tubes. After they had been left to stand for 5 days under laboratory conditions (21° C.), soil and roots were examined for live Diabrotica larvae and the mortality was determined. At 300 ppm (active substance content in the test solution), 100% mortality of the test animals which had been introduced was shown by the preparations of Examples No. 57, 59, 61, 73, 124, 137, 95 and 53.

EXAMPLE R

Field beans (*Vicia faba*) which were severely populated with the black bean aphid *(Aphis fabae)* were sprayed with aqueous dilutions of wettable powder concentrates with an active substance content of 300 ppm to the stage of beginning run-off. The mortality of the aphids was determined after 3 days. A 100% destruction was achieved with the compounds of Examples No. 14, 48, 57, 73, 124, 137, 143, 179, 126, 112 and 163.

EXAMPLE S

Bean plants (Phaseolus v.) which were severely infested with greenhouse red spider mites (*Tetranychus urticae*, full population) were sprayed with the aqueous dilution of a wettable powder concentrate which contained 300 ppm of the active substance in question. The mortality of the mites was checked after 7 days. 100% destruction was achieved with the compounds of Examples No. 57, 73, 137, 141, 95, 166, 126, 112 and 163.

Use as ovicide

EXAMPLE T

Filter paper disks supporting eggs of large milkweed bugs (*Oncopeltus fasciatus*) were each treated with 0.5 ml portions of aqueous dilution of the test formulation. After the coating had dried on, the Petri dish was closed and the inside was kept at maximum atmospheric humidity. After the dishes had been kept at room temperature, the ovicidal activity was determined after 7 days. At an active substance content of 300 ppm, 100% ovicidal activity was achieved by the compounds of Examples No. 13, 14, 15, 38, 39, 40, 48, 52, 57, 59, 61, 73, 124, 137, 147, 174, 175 and 179.

EXAMPLE U

L2 larvae of *Spodoptera littoralis* (Egyptian cotton leafworm) were introduced into Petri dishes, the dishes having been equipped at the bottom with filter paper and containing a small amount of nutrient medium. The dishes with the nutrient medium and the larvae which had been introduced were sprayed with the aqueous emulsions of the test substances, and the Petri dishes were closed with a cover. After 5 days at approximately 23° C., the activity of the compound against the larvae was determined. A 100% activity was achieved with the compounds of Examples No. 57 and 124 at a concentration of 300 ppm (active compound content) in the spray mixture.

Use as antiparasitic

EXAMPLE V

In-vitro test on tropical cattle ticks (*Boophilus microplus*)

The activity of the compounds according to the invention against ticks was demonstrated in the following experimental set-up: To produce a suitable preparation of active substance, the active substances were dissolved at a concentration of 10% (w/v) in a mixture composed of dimethylformamide (85 g), nonylphenol polyglycol ether (3 g) and oxyethylated castor oil (7 g) and the resulting emulsion concentrates were diluted with water to a test concentration of 500 ppm.

Batches of ten female tropical ticks, *Boophilus microplus*, which had sucked themselves full were immersed for five minutes in these dilutions of active substance. The ticks were subsequently dried on filter paper and then attached, with their backs, to an adhesive film in order to deposit eggs. The ticks were kept in an incubator at 28° C. and an atmospheric humidity of 90%.

For the control, female ticks were immersed in water only. The activity was assessed on the basis of the inhibition of egg deposition two weeks after the treatment. In this test, the compounds of Examples No. 56, 57, 59, 60, 179, 112, 163, 115, 113 and 111 caused in each case 100% inhibition of egg deposition.

What is claimed is:

1. A compound of formula I

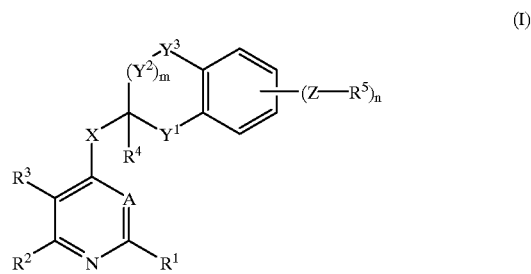

(I)

in which

R¹ is hydrogen, halogen, $(C_1-C_4)$-alkyl, $(C_1-C_4)$-haloalkyl or $(C_3-C_5)$-cycloakyl;

$R_2$ and $R_3$ are identical or different and are in each case hydrogen, $(C_1-C_4)$-alkyl, $(C_1-C_4)$-haloalkyl, $(C_2-C_4)$-alkenyl, $(C_2-C_4)$-haloalkenyl, $(C_2-C_4)$-alkynyl, $(C_2-C_4)$-haloalkynyl, tri-$(C_1-C_4)$-alkylsilyl-$(C_2-C_4)$-alkynyl, $(C_1-C_4)$-alkoxy, $(C_1C_4)$-haloalkoxy, $(C_1-C_4)$-alkoxy-$(C_1C_4)$-alkyl, $(C_1-C_4)$-haloalkoxy-$(C_1-C_4)$-alkyl, $(C_1-C_4)$-alkoxy-$(C_1-C_4)$-haloalkyl, $(C_1-C_4)$-haloalkoxy-$(C_1-C_4)$-haloalkyl, halogen, hydroxyl, $(C_1-C_4)$-hydroxyalkyl, $(C_1-C_4)$-alkanoyl, $(C_1-C_4)$-alkanoyl-$(C_1-C_4)$-alkyl, $(C_2-C_4)$-haloalkanoyl, $(C_3-C_5)$-cycloalkyl, $(C_4-C_5)$-cycloalkenyl, $(C_3-C_5)$-cycloalkoxy, $(C_3-C_5)$-halocycloalkyl, $(C_4-C_5)$- halocycloalkenyl, cyano, $(C_1-C_4)$-cyanoalkyl, nitro, $(C_1-C_4)$-nitroalkly, thiocyano, $(C_1-C_4)$-thiocyanoalkyl, $(C_1-C_4)$-alkoxycarbonyl, $(C_1-C_4)$-alkoxycarbonyl-$(C_1-C_4)$-alkyl, $(C_1-C_4)$-haloalkoxycarbonyl, $(C_1-C_4)$-alkanoyloxy-$(C_1-C_4)$-alkyl, $(C_1-C_4)$-alkylthio, $(C_1-C_4)$-alkylthio-$(C_1-C_4)$-alkyl, $(C_1-C_4)$haloalkylthio, $(C_1-C_4)$-alkylsulfinyl, $(C_1-C_4)$-haloalkylsulfinyl, $(C_1-C_4)$- or $(C_1-C_4)$-haloalkylsulfonoyl;

A is N;

X is NH, O or $S(O)_q$ where q is 0, 1 or 2;

$Y^1 Y^2$ and $Y^3$ independently of one another are a group of he formula —O—, —CO—, —$CNR^6$—, —$S(O)_r$—, —$N(O)_1 R^6$— or $CR^7 R^8$ where r is 0, 1 or 2 and 1 is 0 or 1 or $Y^1$ or $Y^3$ replace a direct bond;

$R^4$ is hydrogen of $(C_1-C_4)$-alkyl;

m is 0 or 1;

n is 0, 1, 2, 3 or 4;

Z is a direct bond, $NR^9$, O, $S(O)_s$ where s is 0, 1 or 2, $OSO_2$, $SO_2 O$, $NR^{10} SO_2$, $SO_2 NR^{11}$, $SiR^{12} R^{13}$, $U^1 P(W^1) V^1 V^2$ or

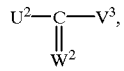

where $U^1$, $U^2$ in dependently of one another are direct bond, $NR^{14}$ or O;

$W^1$, $W^2$ independently of one another are oxygen or sulfur;

$V^1$, $V^2$, $V^3$ independently of one another a direct bond, $NR^{15}$ or oxygen, where $R^9$, $R^{10}$, $R^{11}$, $R^{14}$ and $R^{15}$ are identical or different and are in each case hydrogen alkyl, alkoxy, alkanoyl or cycloalkyl;

$R^5$ radicals are substituents which are independent of one another and are halogen, cyano, nitro, alkyl, alkenyl, alkynyl, cycloalkyl, cycloalkenyl and it being possible for one or more non-adjacent saturated carbon units in the last-mentioned 5 radicals to be replaced by a carbonyl group or by oxygen, $S(O)_x$ where x is 0, 1 or 2, $NR^{16}$ or $SiR^{17} R^{18}$, and wherein these last-mentioned 5 radicals, with or without the above mentioned variations, are optionally substituted by one or more, in the case of fluorine up to the maximum number of identical or different radicals $D^1 R^{19}$, or $R^5$ is aryl or heterocyclyl, it being possible for these two radicals to be unsubstituted or to be substituted by up to three, in the case of fluorine also up to the maximum number of, identical or different radicals $D^2 R^{20}$, or two adjacent radicals Z—$R^5$ together with the carbon atoms to which they are attached can form a fused cycle having 4 to 6 ring atoms which is carbocyclic or contains hetero ring atoms selected from the group consisting of O, S and N and which is unsubstituted of substituted by one or more radicals selected from the group consisting of halogen, $(C_1-C_4)$-alkyl and oxo, or $R^6$, $R^{10}$, $R^{11}$ or $R^{15}$ independently of one another together with the $R^5$ which is attached to Z can be form a 4- to 8-membered ring system in which one or two $CH_2$ groups are optionally replaced by oxygen, $S(O)_t$ where t is 0, 1 or 2 or $NR^{25}$, where $R^6$ is hydrogen, $(C_1-C_4)$-alkyl, $(C_1-C_4)$-haloalkyl, $(C_2-C_4)$-alkenyl, $(C_2-C_4)$-haloalkenyl, $(C_2-C_4)$-alkynyl, $(C_2-C_4)$-haloalkynyl, $(C_1-C_4)$-alkoxy, $(C_1-C_4)$-haloalkoxy, $(C_1 C_4)$-alkythio, $(C_1-C_4)$-haloalkylthio, $(C_1-C_4)$-alkanoyl, $(C_2-C_4)$-haloalkanoyl, $(C_3-C_5)$-cycloalkyl, $(C_1-C_4,)$-alkylsulfonyl, $(C_1-C_4)$haloalkylsulfonyl, $(C_1-C_4)$-alkoxy-$(C_1-C_4)$-alkyl, $(C_1-C_4)$-alkoxycarbonyl;

$R^7$ and $R^8$ independently of one another are hydrogen, hydroxyl, halogen, cyano, $(C_1-C_4)$-alkyl, $(C_1-C_4)$-haloalkyl, $(C_2-C_4)$-alkenyl, $(C_2-C_4)$-haloalkenyl, $(C_2-C_4)$-alkynyl, $(C_2-C_4)$-haloalkenyl, $(C_3-C_5)$-cycloalkyl, $(C_1-C_4)$-alkanoyl, $(C_1-C_4)$-haloalkanoyl, $(C_1-C_4)$-alkoxy, $(C_1-C_4)$-haloalkoxy, $(C_1-C_4)$-haloalkoxy, $(C_1-C_4)$-alkylthio or $(C_1-C_4)$-haloalkylthio;

$R^{12}$ and $R^{13}$ independently of one another are $(C_1-C_4)$-alkyl or phenyl;

$R^{16}$ is hydrogen, $(C_1-C_4)$-alkyl, $(C_1-C_4)$-alkoxy or $(C_1-C_4)$-alkanoyl;

$R^{17}$ and $R^{18}$ independently of one another are $(C_1-C_4)$-alkyl, $D^1$ and $D^2$ are in each case independent of one another and are a direct bond, oxygen, $S(O)_k$, $SO_2 O$, $OSO_2$, CO, OCO, COO, $NR^{21}$, $SO_2 NR^{21}$, $NR^{21} SO_2$, $ONR^{21}$, $NR^{21} O$ $NR^{21} CO$, $CONR^{21}$ or $SiR^{22} R^{23}$ and k is 0, 1 or 2, where $R^{21}$ radicals independently of one another are hydrogen, $(C_1-C_4)$-alkyl, $(C_1-C_4)$-alkanoyl or $(C_3-C_5)$-cycloalkyl;

$R^{22}$ and $R^{23}$ independently of one another are $(C_1-C_4)$-alkyl;

$R^{19}$ and $R^{20}$ independently of one another are hydrogen, cyano, nitro, halogen, alkyl, haloalkyl, alkenyl, haloalkenyl, alkynyl, haloalkynl, alkoxyalkyl, haloalkoxyalkyl, alklylthioalkyl, haloalkylthioalkyl, cycloalkyl, cycloalkenyl, cycloalkylalkyl, cycloalkenylalkyl, aryl, heterocyclyl, aryalkyl or heterocyclyalkyl, the cycloalipathic, aromatic or heterocyclic ring systems in the last-mentioned 8 radicals being unsubstituted or substituted or with one to three, in the case of fluorine also up to the maximum number of, identical or different substituents $R^{24}$, or $R^{19}$ and $R^{20}$, attached to the same carbon atom, together are an oxo group; where $R^{24}$ radicals independently of one another are $(C_1-C_4)$-alkyl, $(C_1-C_4)$-haloalkyl, $(C_1-C_4)$-alkoxy, $(C_1-C_4)$-haloalkoxy, cyano, nitro or halogen;

$R^{25}$ independently of one another are hydrogen, $(C_1-C_8)$-alkyl, $(C_1-C_4)$-haloalkyl, $(C_1-C_4)$-alkoxy, $(C_1-C_4)$-alkylthio, $(C_3-C_5)$-cycloalkyl, $(C_2-C_4)$-alkenyl, $(C_2-C_4)$-alkynyl, $(C_1-C_4)$-alkanoyl, $(C_1-C_4)$-haloalkanoyl, $(C_1-C_4)$-alkoxy-$(C_1-C_4)$-alkyl, phenyl-$(C_1-C_4)$-alkyl or phenyl, the phenyl groups independently of one another being unsubstituted or being provided with up to three, in the case of fluorine also up to the maximum number of, identical or different substituents $R^{26}$, where $R^{26}$ substituents independently of one another are $(C_1-C_4)$-alkyl, $(C_1-C_4)$-haloalkyl, $(C_1-C_4)$-alkoxy, $(C_1-C_4)$-alkylthio, halogen or cyano, or a salt thereof.

2. A compound of the formula I as claimed in claim 1 in which $R^1$ is hydrogen, halogen, $(C_1-C_4)$-alkyl, $(C_1-C_4)$-haloalkyl or $(C_3-C_5)$-cycloalkyl;

$R^2$ and $R^3$ are identical or different and are in each case hydrogen, $(C_1-C_4)$-alkyl, $(C_1-C_4)$-haloalkyl, $(C_2-C_4)$-alkenyl, $(C_2-C_4)$-haloalkenyl, $(C_2-C_4)$-alkynyl, $(C_2-C_4)$-haloalkynyl, tri-$(C_1-C_4)$-alkylsilyl-$(C_2-C_4)$-alkynyl, $(C_1-C_4)$-alkoxy, $(C_1-C_4)$-haloalkoxy, $(C_1-C_4)$-alkoxy-$(C_1-C_4)$-alkyl, $(C_1-C_4)$-haloalkoxy-$(C_1-C_4)$-alkyl, $(C_1-C_4)$-alkoxy-$(C_1-C_4)$-haloalkyl, $(C_1-C_4)$-haloalkoxy-$(C_1-C_4)$-haloalkyl, halogen, hydroxyl, $(C_1-C_4)$-hydroxyalkyl, $(C_1-C_4)$-alkanoyl, $(C_1-C_4)$-alkanoyl-$(C_1-C_4)$-alkyl, $(C_2-C_4)$-haloalkanoyl, $(C_3-C_5)$-cycloalkyl, $(C_4-C_5)$-cycloalkenyl, $(C_3-C_5)$-cycloalkoxy, $(C_3-C_5)$-halocycloalkyl, $(C_4-C_5)$-halocycloalkenyl, cyano, $(C_1-C_4)$-cyanoalkyl, nitro, $(C_1-C_4)$-nitroalkyl, thiocyano, $(C_1-C_4)$-thiocyanoalkyl, $(C_1-C_4)$-alkoxycarbonyl, $(C_1-C_4)$-alkoxycarbonyl-$(C_1-C_4)$-alkyl, $(C_1-C_4)$-haloalkoxycarbonyl, $(C_1-C_4)$-alkanoyloxy-$(C_1-C_4)$-alkyl, $(C_1-C_4)$-alkylthio, $(C_1-C_4)$-alkylthio-$(C_1-C_4)$-alkyl, $(C_1-C_4)$-haloalkylthio, $(C_1-C_4)$-alkylsulfinyl, $(C_1-C_4)$-haloalkylsulfinyl, $(C_1-C_4)$-alkylsulfonyl or $(C_1-C_4)$-haloalkylsulfonyl;

A is N;

X is NH, O or $S(O)_q$ where q is 0, 1 or 2;

$Y^1$, $Y^2$ and $Y^3$ independently of one another are a group of the formula —O—, —S(O)$_r$—, —N(O)$_l$R$^6$— or $CR^7R^8$ where r is =0, 1 or 2 and l is 0 or 1; or $Y^1$ or $Y^3$ replace a direct bond;

$Ry^4$ is hydrogen or $(C_1-C_4)$-alkyl;

m is 1;

n is 1 or 2;

Z is a direct bond, $NR^9$, O, $S(O)_s$ where s is 0, 1 or 2, $OSO_2$, $SO_2O$, $NR^{10}SO_2$, $SO_2NR^{11}$, $SiR^{12}R^{13}$, $U^1P(W^1)V^1V^2$ or

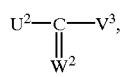

where $U^1$, $U^2$ independently of one another are a direct bond, $NR^{14}$ or O;

$W^1$, $W^2$ independently of one another are oxygen or sulfur;

$V^1$, $V^2$, $V^3$ independently of one another are a direct bond, $NR^{15}$ or oxygen, where $R^9$, $R^{10}$, $R^{11}$, $R^{14}$ and $R^{15}$ are identical or different and are in each case hydrogen, alkyl, alkoxy, alkanoyl or cycloalkyl;

$R^5$ radicals are substituents which are independent of one another and are halogen, cyano, nitro, alkyl, alkenyl, alkynyl, cycloalkyl, cycloalkenyl and where up to three non-adjacent saturated carbon units in the last-mentioned 5 radicals are replaced by a carbonyl group or by oxygen, $S(O)_x$ where x is 0, 1 or 2, $NR^{16}$ or $SiR^{17}R^{18}$, and where the last-mentioned 5 radicals, with or without the abovementioned variations, are optionally substituted by one to three, in the case of fluorine up to the maximum number of, identical or different radicals $D^1R^{19}$, or $R^5$ is aryl or heterocyclyl, where these two radicals are optionally substituted by one to three, in the case of fluorine also up to the maximum number of, identical or different radicals $D^2R^{20}$, or two adjacent radicals $Z—R^5$ together with the carbon atoms to which they are attached form a fused cycle having 4 to 6 ring atoms which is carbocyclic or contains hetero ring atoms selected from the group consisting of O, S and N and which is unsubstituted or substituted by one or more radicals selected from the group consisting of halogen, $(C_1-C_4)$-alkyl and oxo, or $R^9$, $R^{10}$, $R^{11}$, $R^{14}$ or $R^{15}$ independently of one another together with the $R^5$ which is attached to Z form a 4- to 8-membered ring system in which a $CH_2$ group is optionally replaced by oxygen, $S(O)_t$ where t is 0, 1 or 2 or $NR^{25}$, where $R^6$ is hydrogen, $(C_1-C_4)$-alkyl, $(C_1-C_4)$-haloalkyl, $(C_2-C_4)$-alkenyl, $(C_2-C_4)$-haloalkenyl, $(C_2-C_4)$-alkynyl, $(C_2-C_4)$-haloalkynyl, $(C_1-C_4)$-alkoxy, $(C_1-C_4)$-haloalkoxy, $(C_1-C_4)$-alkylthio, $(C_1-C_4)$-haloalkylthio, $(C_1-C_4)$-alkanoyl, $(C_2-C_4)$-haloalkanoyl, $(C_3-C_5)$-cycloalkyl, $(C_1-C_4)$-alkylsulfonyl, $(C_1-C_4)$-haloalkylsulfonyl, $(C_1-C_4)$-alkoxy-$(C_1-C_4)$-alkyl, $(C_1-C_4)$-alkoxycarbonyl;

$R^7$ and $R^8$ independently of one another are hydrogen, hydroxyl, halogen, cyano, $(C_1-C_4)$-alkyl, $(C_1-C_4)$-haloalkyl, $(C_2-C_4)$-alkenyl, $(C_2-C_4)$-haloalkenyl, $(C_2-C_4)$-alkynyl, $(C_2-C_4)$-haloalkynyl, $(C_3-C_5)$-cycloalkyl, $(C_1-C_4)$-alkanoyl, $(C_1-C_4)$-haloalkanoyl, $(C_1-C_4)$-alkoxy, $(C_1-C_4)$-haloalkoxy, $(C_1-C_4)$-alkylthio or $(C_1-C_4)$-haloalkylthio;

$R^{12}$ and $R^{13}$ are methyl;

$R^{16}$ is hydrogen, $(C_1-C_4)$-alkyl, $(C_1-C_4)$-alkoxy or $(C_1-C_4)$-alkanoyl;

$R^{17}$ and $R^{18}$ are methyl;

$D^1$ and $D^2$ are in each case independent of one another and are a direct bond, oxygen, $S(O)_k$, $SO_2O$, $OSO_2$, CO, OCO, COO, $NR^{21}$, $SO_2NR^{21}$, $NR^{21}SO_2$, $ONR^{21}$, $NR^{21}O$, $NR^{21}CO$, $CONR^{21}$ or $SiR^{22}R^{23}$ and k is 0, 1 or 2, where $R^{21}$ radicals independently of one another are hydrogen, $(C_1-C_4)$-alkyl, $(C_1-C_4)$-alkanoyl or $(C_3-C_5)$-cycloalkyl;

$R^{22}$ and $R^{23}$ independently of one another are $(C_1-C_4)$-alkyl;

$R^{19}$ and $R^{20}$ independently of one another are hydrogen, cyano, nitro, halogen, alkyl, haloalkyl, alkenyl, haloalkenyl, alkynyl, haloalkynyl, alkoxyalkyl, haloalkoxyalkyl, alkylthioalkyl, haloalkylthioalkyl, cycloalkyl, cycloalkenyl, cycloalkylalkyl, cycloalkenylalkyl, aryl, heterocyclyl, arylalkyl or heterocyclyalkyl, the cycloaliphatic, aromatic or heterocyclic ring systems in last-mentioned 8 radicals are unsubstituted or substituted with one to three, in the case of fluorine also up to the maximum number of, identical or different substituents $R^{24}$, or $R^{19}$ and $R^{20}$, attached to the same carbon atom, together are an oxo group; where $R^{24}$ radicals independently of one another are $(C_1-C_4)$-alkyl, $(C_1-C_4)$-haloalkyl, $(C_1-C_4)$-alkoxy, $(C_1-C_4)$-haloalkoxy, cyano, nitro or halogen;

$R^{25}$ independently of one another are hydrogen, $(C_1-C_8)$-alkyl, $(C_1-C_4)$-haloalkyl, $(C_1-C_4)$-alkoxy, $(C_1-C_4)$-alkylthio, $(C_3-C_5)$-cycloalkyl, $(C_2-C_4)$-alkenyl, $(C_2-C_4)$-alkynyl, $(C_1-C_4)$-alkanoyl, $(C_1-C_4)$-haloalkanoyl, $(C_1-C_4)$-alkoxy-$(C_1-C_4)$-alkyl, phenyl-$(C_1-C_4)$-alkyl or phenyl, the phenyl groups independently of one another are unsubstituted or substituted with one to three, in the case or fluorine also up to the maximum number of, identical or different substituents $R^{26}$, where $R^{26}$ substituents independently of one another are $(C_1-C_4)$-alkyl, $(C_1-C_4)$-haloalkyl, $(C_1-C_4)$-alkoxy, $(C_1-C_4)$-alkylthio, halogen or cyano, or a salt thereof.

3. A compound of the formula I as claimed in claim 1 in which $R^5$ radicals are substituents which are independent of one another and are halogen, cyano, nitro, $(C_1-C_{20})$-alkyl; $(C_2-C_{20})$-alkenyl, $(C_2-C_{20})$-alkynyl, $(C_3-C_8)$-cycloalkyl, $(C_4-C_8)$-cycloalkenyl and one or more non-adjacent saturated carbon units in the last-mentioned 5 radicals are optionally replaced by a carbonyl group or by oxygen, $S(O)_x$ where x is 0, 1 or 2, $NR^{16}$ or $SiR^{17}R^{18}$ and wherein these last mentioned 5 radicals, with or without the abovementioned variations, are optionally substituted by one or more, in the case of fluorine up to the maximum number of identical or different radicals $D^1R^{19}$, or $R^5$ is aryl or heterocyclyl, wherein these two radicals are unsubstituted or substituted one to three, in the case of fluorine also up to the maximum number of, identical or different radicals $D^2R^{20}$, or two adjacent radicals $R^9$, $R^{11}$ or $R^{15}$ independently of one another together with the $R^5$ attached to Z form a 4- to 8-membered ring system in which one or two $CH_2$ groups are replaced by oxygen, $S(O)_t$ where t is 0, 1 or 2 or $NR^{25}$, where $R^{16}$ is hydrogen, $(C_1-C_4)$-alkyl, $(C_1-C_4)$-alkoxy or $(C_1-C_4)$-alkanoyl;

$R^{17}$ and $R^{18}$ independently of one another are $(C_1-C_4)$-alkyl;

$D^1$ and $D^2$ are in each case independent of one another and are a direct bond, oxygen, $S(O)_k$, $SO_2O$, $OSO_2$, CO, OCO, COO, $NR^{21}$, $SO_2NR^{21}$, $NR^{21}SO_2$, $ONR^{21}$, $NR^{21}O$, $NR^{21}CO$, $CONR^{21}$ or $SiR^{22}R^{23}$ and k is 0, 1 or 2, where $R^{21}$ radicals independently of one another are hydrogen, $(C_1-C_4)$-alkyl, $(C_1-C_4)$-alkanoyl or $(C_3-C_5)$-cycloalkyl;

$R^{22}$ and $R^{23}$ independently of one another are $(C_1-C_4)$-alkyl;

$R^{19}$ and $R^{20}$ independently of one another are hydrogen, cyano, nitro, halogen, $(C_1-C_8)$-alkyl, $(C_1-C_8)$-haloalkyl, $(C_2-C_8)$-alkenyl, $(C_2-C_8)$-haloalkenyl, $(C_2-C_8)$-alkynyl, $(C_2-C_8)$-haloalkynyl, $(C_1-C_8)$-alkoxy-$(C_1-C_4)$-alkyl, $(C_1-C_8)$-haloalkoxy-$(C_1-C_4)$-alkyl, $(C_1-C_8)$-alkylthio-$(C_1-C_4)$-alkyl, $(C_1-C_8)$-haloalkylthio-$(C_1-C_4)$-alkyl, $(C_3-C_8)$-cycloalkyl, $(C_4-C_8)$-cycloalkenyl, $(C_3-C_8)$-cycloalkyl-$(C_1-C_4)$-alkyl, $(C_4-C_8)$-cycloalkenyl-$(C_1-C_4)$-alkyl, aryl, heterocyclyl, aryl-$(C_1-C_4)$-alkyl or heterocyclyl-$(C_1-C_4)$-alkyl, where, in the last-mentioned 8 radicals, the cycloaliphatic aromatic or heterocyclic ring systems are unsubstituted or substituted one to three, in the case of fluorine also up to the maximum number of, identical or different substituents $R^{24}$, or $R^{19}$ and $R^{20}$, attached to the same carbon atom, together are an oxo group, where $R^{24}$ radicals independently of one another are $(C_1-C_4)$-alkyl, $(C_1-C_4)$-haloalkyl, $(C_1-C_4)$-alkoxy, $(C_1-C_4)$-haloalkoxy, cyano, nitro or halogen;

$R^{25}$ radicals are hydrogen, $(C_1-C_8)$-alkyl, $(C_1-C_4)$-haloalkyl, $(C_1-C_4)$-alkoxy, $(C_1-C_4)$-alkylthio, $(C_3-C_5)$-cycloalkyl, $(C_2-C_4)$-alkenyl, $(C_2-C_4)$-alkynyl, $(C_1-C_4)$-alkanoyl, $(C_2-C_4)$-haloalkanoyl, $(C_2-C_4)$-alkoxyalkyl, phenyl-$(C_1-C_4)$-alkyl or phenyl and the phenyl groups independently of one another are unsubstituted or substituted one to three, in the case of fluorine also up to the maximum number of, identical or different substituents $R^{26}$, where $R^{26}$ radicals independently of one another are $(C_1-C_4)$-alkyl, $(C_1-C_4)$-haloalkyl, $(C_1-C_4)$-alkoxy, $(C_1-C_4)$-alkylthio, halogen or cyano, or a salt thereof.

4. A compound of the formula I as claimed in claim 1 where $R^5$ radicals are substituents which are independent of one another and are halogen, cyano, nitro, $(C_1-C_{20})$-alkyl, $(C_2-C_{20})$-alkenyl, $(C_2-C_{20})$-alkynyl, $(C_3-C_8)$-cycloalkyl, $(C_4-C_8)$-cycloalkenyl and up to three non-adjacent saturated carbon units in the last-mentioned 5 radicals are optionally replaced by a carbonyl group or by oxygen, $S(O)_x$ where x is 0, 1 or 2, $NR^{16}$ or $SiR^{17}R^{18}$ and wherein these last-mentioned 5 radicals, with or without the abovementioned variations, are optionally substituted by one to three, in the case of fluorine up to the maximum number of, identical or different radicals $D^1R^{19}$, or $R^5$ is aryl or heterocyclyl, wherein these two radicals to be unsubstituted or to be substituted by one to three, in the case of fluorine also up to the maximum number of, identical or different radicals $D^2R^{20}$, or two adjacent radicals Z—$R^5$ together with the carbon atoms to which they are attached form a fused cycle having 4 to 6 ring atoms which is carbocyclic or contains hetero ring atoms selected from the group consisting of O, S and N and which is unsubstituted or substituted by one or more radicals selected from the group consisting of halogen, $(C_1-C_4)$-alkyl and oxo, or $R^9$, $R^{11}$ or $R^{15}$ independently of one another together with the $R^5$ attached to Z form a 4- to 8-membered ring system in which one $CH_2$ group is replaced by oxygen, $S(O)_t$ where t is 0, 1 or 2 or $NR^{25}$, where $R^{16}$ is hydrogen, $(C_1-C_4)$-alkyl, $(C_1-C_4)$-alkoxy or $(C_1-C_4)$-alkanoyl;

$R^{17}$ and $R^{18}$ are methyl;

$D^1$ and $D^2$ are in each case independent of one another and are a direct bond, oxygen, $S(O)_k$, $SO_2O$, $OSO_2$, CO, OCO, COO, $NR^{21}$, $SO_2NR^{21}$, $NR^{21}SO_2$, $ONR^{21}$, $NR^{21}O$, $NR^{21}CO$, $CONR^{21}$ or $SiR^{22}R^{23}$ and k is 0, 1 or 2, where $R^{21}$ radicals independently of one another are hydrogen, $(C_1-C_4)$-alkyl, $(C_1-C_4)$-alkanoyl or $(C_3-C_5)$-cycloalkyl;

$R^{22}$ and $R^{23}$ independently of one another are $(C_1-C_4)$-alkyl;

$R^{19}$ and $R^{20}$ independently of one another are hydrogen, cyano, nitro, halogen, $(C_1-C_8)$-alkyl, $(C_1-C_8)$-haloalkyl, $(C_2-C_8)$-alkenyl, $(C_2-C_8)$-haloalkenyl, $(C_2-C_8)$-alkynyl, $(C_2-C_8)$-haloalkynyl, $(C_1-C_8)$-alkoxy-$(C_1-C_4)$-alkyl, $(C_1-C_8)$-haloalkoxy-$(C_1-C_4)$-alkyl, $(C_1-C_8)$-alkylthio-$(C_1-C_4)$-alkyl, $(C_1-C_8)$-haloalkylthio-$(C_1-C_4)$-alkyl, $(C_3-C_8)$-cycloalkyl, $(C_4-C_8)$-cycloalkenyl, $(C_3-C_8)$-cycloalkyl-$(C_1-C_4)$-alkyl, $(C_4-C_8)$-cycloalkenyl-$(C_1-C_4)$-alkyl, aryl, heterocyclyl, aryl-$(C_1-C_4)$-alkyl or heterocyclyl-$(C_1-C_4)$-alkyl, where, in the last-mentioned 8 radicals the cycloaliphatic, aromatic or heterocyclic ring systems are unsubstituted or substituted one to three, in the case of fluorine also up to the maximum number of, identical or different substituents $R^{24}$, or $R^{19}$ and $R^{20}$, attached to the same carbon atom, together are an oxo group, where $R^{24}$ radicals independently of one another are $(C_1-C_4)$-alkyl, $(C_1-C_4)$-haloalkyl, $(C_1-C_4)$-alkoxy, $(C_1-C_4)$-haloalkoxy, cyano, nitro or halogen;

$R^{25}$ radicals are independently of one another hydrogen, $(C_1-C_8)$-alkyl, $(C_1-C_4)$-haloalkyl, $(C_1-C_4)$-alkoxy, $(C_1-C_4)$-alkylthio, $(C_3-C_5)$-cycloalkyl, $(C_2-C_4)$-alkenyl, $(C_2-C_4)$-alkynyl, $(C_1-C_4)$-alkanoyl, $(C_2-C_4)$-haloalkanoyl, $(C_2-C_4)$-alkoxyalky, phenyl-$(C_1-C_4)$-alkyl or phenyl and the phenyl groups are unsubstituted or substituted one to three, in the case of fluorine also up to the maximum number of, identical or different substituents $R^{26}$, where $R^{26}$ radicals independently of one another are $(C_1-C_4)$-alkyl, $(C_1-C_4)$-haloalkyl, $(C_1-C_4)$-alkoxy, $(C_1-C_4)$-alkylthio, halogen or cyano, or a salt thereof.

5. A compound of the formula I as claimed in claim 1 where $R^1$ is hydrogen, chlorine or fluorine;

$R^2$ is $(C_1-C_4)$-alkyl, $(C_2-C_4)$-alkenyl, $(C_2-C_4)$-alkynyl, tri-$(C_1-C_4)$-alkylsilyl-$(C_2-C_4)$-alkynyl, $(C_1-C_4)$-haloalkyl, cyclopropyl, halocyclopropyl, methoxymethyl or cyano;

$R^3$ is hydrogen, halogen, methyl, ethyl, ethenyl, ethynyl, methoxy, ethoxy, cyano, trifluoromethyl, fluoromethylthio or methoxycarbonyl;

A is N;

X is NH or oxygen;

$Y^1$, $Y^2$ and $Y^3$ are a group of the formula —O—, —S(O)$_r$—, —N(O)$_l$R$^6$— where l is 0 or 1 and where r is 0, 1 or 2, or are a group of the formula CR$^7$R$^8$; or $Y^1$ or $Y^2$ replace a direct bond;

$R_4$ is hydrogen;

m is 1;

n is 1 or 2;

Z is a direct bond, NR$^9$, O, S(O)$_s$ where s is 0, 1 or 2, or OSO$_2$, SO$_2$O, NR$^{10}$SO$_2$, SO$_2$NR$^{11}$, SiR$^{12}$R$^{13}$, UP(W$^1$)V$^1$V$^2$ or

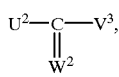

where $U^1$, $U^2$ independently of one another are a direct bond, NR$^{14}$ or O;

$W^1$, $W^2$ are oxygen;

$V^1$, $V^2$, $V^3$ independently of one another are a direct bond, NR$^{15}$ or oxygen; where $R^6$ radicals independently of one another are $(C_1-C_4)$-alkyl or $(C_1-C_4)$-alkanoyl;

$R^7$ and $R^8$ independently of one another are hydrogen, halogen or $(C_1-C_4)$-alkyl, and $R^9$, $R^{10}$, $R^{11}$, $R^{14}$ and $R^{15}$ are identical or different and are in each case hydrogen, $(C_1-C_4)$-alkyl, $(C_1-C_4)$-alkoxy, $(C_1-C_4)$-alkanoyl or $(C_3-C_5)$-cycloalkyl, or a salt thereof.

6. A compound of the formula I as claimed in claim 1 where $R^1$ is hydrogen or fluorine;

$R^2$ is methyl, ethyl, propyl, isopropyl, $(C_1-C_2)$-fluoroalkyl or methoxymethyl;

$R^3$ is halogen, methyl, ethyl, ethenyl, ethynyl, methoxy, ethoxy, trifluoromethyl, fluoromethylthio, methoxycarbonyl or cyano;

A is N;

X is NH or oxygen;

$Y^1$, $Y^2$ and $Y^3$ are a group of the formula —O—, or —S(O)$_r$—, where r is 0, 1 or 2, or a group of the formula CR$^7$R$^8$, or $Y^1$ or $Y^3$ replace a direct bond, where $R^7$ and $R^8$ independently of one another are hydrogen or methyl, or a salt thereof.

7. Compound of the formula I as claimed in claim 1 where $R^1$ is hydrogen;

$R^2$ is ethyl, propyl, isopropyl, 1-fluoroethyl or methoxymethyl;

$R^3$ is fluorine, chlorine, bromine, cyano, methoxy, ethenyl or ethynyl;

or a salt thereof.

8. A compound of the formula I as claimed in claim 1 where $R^1$ is hydrogen;

$R^2$ is ethyl or methoxymethyl;

$R^3$ is fluorine, chlorine, bromine or methoxy;

$R^5$ radicals are substituents which are independent of one another and are halogen, cyano, nitro, $(C_1-C_8)$-alkyl, $(C_2-C_8)$-alkenyl, $(C_2-C_8)$-alkynyl, $(C_3-C_8)$-cycloalkyl, $(C_4-C_8)$-cycloalkenyl and wherein one to three, non-adjacent saturated carbon units in the last-mentioned 5 radicals are optionally replaced by a carbonyl group or by oxygen, S(O)$_x$ where x is 0, 1 or 2, NR$^{16}$ or SiR$^{17}$R$^{18}$, and these last-mentioned 5 radicals, with or without the abovementioned variations, are optionally substituted by one to three, in the case of fluorine up to the maximum number of, identical or different radicals D$^1$R$^{19}$, or $R^5$ is aryl or heterocyclyl, wherein these two radicals are unsubstituted or substituted by one to three, in the case of fluorine also up to the maximum number of, identical or different radicals D$^2$R$^{20}$, or two adjacent radicals Z—R$^5$ together with the carbon atoms to which they are attached form a fused cycle having 4 to 6 ring atoms which is carbocyclic or contains hetero ring atoms selected from the group consisting of O, S and N and which is unsubstituted or substituted by one or more radicals selected from the group consisting of halogen, $(C_1-C_4)$-alkyl and oxo, or $R^{11}$ or $R^{15}$ independently of one another together with the $R^5$ which is attached to Z form a 4- to 8-membered ring system in which one or two CH$_2$ groups, preferably one CH$_2$ group, are replaced by hetero atom units such as oxygen, S(O)$_t$ where t is 0, 1 or 2 or NR$^{25}$, where $R^{16}$ radicals independently of one another are hydrogen, $(C_1-C_4)$-alkyl, $(C_1-C_4)$-alkoxy or $(C_1-C_4)$-alkanoyl;

$R^{17}$ and $R^{18}$ independently of one another are $(C_1-C_4)$-alkyl;

$D^1$ and $D^2$ are in each case independent of one another and are a direct bond, —O—, —S(O)$_k$—, —$SO_2O$—, —$OSO_2$—, —CO—, —OCO—, —COO—, —$NR^{21}$—, —$SO_2NR^{21}$—, —$NR^{21}SO_2$—, —$ONR^{21}$—, —$NR^{21}O$—, —$NR^{21}CO$—, —$CONR^{21}$—, and k is 0, 1 or 2, and where $R^{21}$ radicals independently of one another are hydrogen, $(C_1–C_4)$-alkyl, $(C_1–C_4)$-alkanoyl or $(C_3–C_5)$-cycloalkyl;

$R^{19}$ and $R^{20}$ independently of one another are hydrogen, halogen, preferably fluorine, $(C_1–C_8)$-alkyl, $(C_3–C_8)$-cycloalkyl, aryl or heterocyclyl, the cycloaliphatic, aromatic or heterocyclic ring systems in the last-mentioned three radicals being unsubstituted or substituted one to three, in the case of fluorine also up to the maximum number of, identical or different substituents $R^{24}$, where $R^{24}$ radicals independently of one another are $(C_1–C_4)$-alkyl, $(C_1–C_4)$-haloalkyl, $(C_1–C_4)$-alkoxy, $(C_1–C_4)$-haloalkoxy, cyano, nitro or halogen;

$R^{25}$ radicals independently of one another are $(C_1–C_8)$-alkyl, $(C_3–C_5)$-cycloalkyl, $(C_1–C_4)$-alkanoyl, $(C_2–C_4)$-haloalkanoyl, $(C_1–C_4)$-alkoxy-$(C_1–C_4)$-alkyl, phenyl-$(C_1–C_4)$-alkyl or phenyl and the phenyl groups independently of one another are unsubstituted or substituted one to three, in the case of fluorine also up to the maximum number of, identical or different substituents $R^{26}$, where $R^{26}$ radicals independently of one another are $(C_1–C_4)$-alkyl, $(C_1–C_4)$-haloalkyl, $(C_1–C_4)$-alkoxy, $(C_1–C_4)$-alkylthio, halogen or cyano, or a salt thereof.

9. A compound of the formula I as claimed in claim 1 where $R^5$ is as defined in claim 1 wherein one to three, non-adjacent saturated carbon units are optionally replaced by oxygen and which, with or without the abovementioned variations, are optionally substituted by one to three, in the case of fluorine up to the maximum number of, identical or different radicals $D^1R^9$, or $R^5$ is aryl or heterocyclyl, wherein these two radicals are unsubstituted or substituted by one to three, in the case of fluorine also up to the maximum number of, identical or different radicals $D^2R^{20}$, or a salt thereof.

10. A composition comprising a compound as claimed in 1 and at least one formulation auxiliary.

11. A method of controlling endo- or ectoparasites, which comprises administering such an amount of a compound as claimed in claim 1 as is effective for this application.

12. A method of controlling phytopathogenic fungi, which comprises applying a fungicidally active amount of a compound as claimed in claim 1 to these phytopathogenic fungi or to the plants, areas or substrates infested with them, or to seed.

13. A method of controlling insects, Acarina, molluscs, nematodes or eggs of these, which comprises applying an insecticidally, acaricidally, ixodicidally, nematicidally or ovicidally active amount of a compound as claimed in claim 1 to these insects, Acarina, molluscs, nematodes or eggs of these or to the plants, areas or substrates infested with them.

* * * * *